(12) United States Patent
Kato et al.

(10) Patent No.: US 9,807,361 B2
(45) Date of Patent: Oct. 31, 2017

(54) THREE-DIMENSIONAL DISPLAY DEVICE, THREE-DIMENSIONAL IMAGE PROCESSING DEVICE, AND THREE-DIMENSIONAL DISPLAY METHOD

(71) Applicant: Panasonic Corporation, Osaka (JP)

(72) Inventors: Yumiko Kato, Osaka (JP); Jun Ozawa, Nara (JP); Tsuyoshi Inoue, Nara (JP); Toru Nakada, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 591 days.

(21) Appl. No.: 14/297,018

(22) Filed: Jun. 5, 2014

(65) Prior Publication Data

US 2014/0285641 A1    Sep. 25, 2014

Related U.S. Application Data

(63) Continuation of application No. PCT/JP2013/005666, filed on Sep. 25, 2013.

(30) Foreign Application Priority Data

Oct. 9, 2012  (JP) .................................. 2012-224565

(51) Int. Cl.
*H04N 13/00*     (2006.01)
*G06F 3/01*      (2006.01)
(Continued)

(52) U.S. Cl.
CPC ....... *H04N 13/0018* (2013.01); *A61B 5/0496* (2013.01); *A61B 5/742* (2013.01);
(Continued)

(58) Field of Classification Search
CPC ............................ H04N 13/0018; A61B 5/742
(Continued)

(56) References Cited

U.S. PATENT DOCUMENTS

| 5,726,704 A | 3/1998 | Uomori |
| 5,801,760 A | 9/1998 | Uomori |

(Continued)

FOREIGN PATENT DOCUMENTS

| JP | 7-167633 | 7/1995 |
| JP | 10-83460 | 3/1998 |

(Continued)

OTHER PUBLICATIONS

International Search Report issued in International Application No. PCT/JP2013/005666 on Nov. 19, 2013.

*Primary Examiner* — Jeffery Williams
(74) *Attorney, Agent, or Firm* — Wenderoth, Lind & Ponack, L.L.P.

(57) ABSTRACT

A three-dimensional display device for displaying a three-dimensional image, including: a gaze point obtaining unit which obtains a position of a gaze point of a viewer; a fusional area determination unit which determines a fusional area where binocular fusion is allowed, based on the obtained position of the gaze point; a correction unit which corrects the three-dimensional image so as to suppress display of an object that is included in the three-dimensional image outside the fusional area; and a display unit which displays the corrected three-dimensional image.

13 Claims, 35 Drawing Sheets

(51) Int. Cl.
  *G06T 19/00* (2011.01)
  *A61B 5/00* (2006.01)
  *G09G 3/00* (2006.01)
  *H04N 13/04* (2006.01)
  *A61B 5/0496* (2006.01)
  *A61B 5/02* (2006.01)

(52) U.S. Cl.
  CPC .............. *G06F 3/013* (2013.01); *G06T 19/00* (2013.01); *G09G 3/003* (2013.01); *H04N 13/0007* (2013.01); *H04N 13/0022* (2013.01); *H04N 13/0484* (2013.01); *A61B 5/02007* (2013.01); *A61B 5/6821* (2013.01); *G06T 2210/41* (2013.01); *G09G 2340/10* (2013.01)

(58) Field of Classification Search
  USPC .......................................................... 348/54
  See application file for complete search history.

(56) References Cited

U.S. PATENT DOCUMENTS

| | | | |
|---|---|---|---|
| 6,175,379 B1 * | 1/2001 | Uomori | H04N 13/0278 345/419 |
| 6,198,484 B1 | 3/2001 | Kameyama | |
| 6,414,681 B1 * | 7/2002 | Ohshima | G06F 3/012 345/428 |
| 7,486,817 B2 | 2/2009 | Yanagawa et al. | |
| 2005/0195478 A1 | 9/2005 | Yanagawa et al. | |
| 2009/0002483 A1 | 1/2009 | Yanagawa et al. | |
| 2009/0262184 A1 * | 10/2009 | Engle | G06T 19/00 348/47 |
| 2011/0292183 A1 | 12/2011 | Tajiri et al. | |
| 2013/0100153 A1 * | 4/2013 | Taguchi | G06T 19/20 345/589 |
| 2013/0100257 A1 * | 4/2013 | Sawachi | H04N 13/0246 348/49 |

FOREIGN PATENT DOCUMENTS

| | | |
|---|---|---|
| JP | 2001-84409 | 3/2001 |
| JP | 2005-252459 | 9/2005 |
| JP | 2011-248693 | 12/2011 |
| WO | 2010/021309 | 2/2010 |

* cited by examiner

FIG. 1
(a)
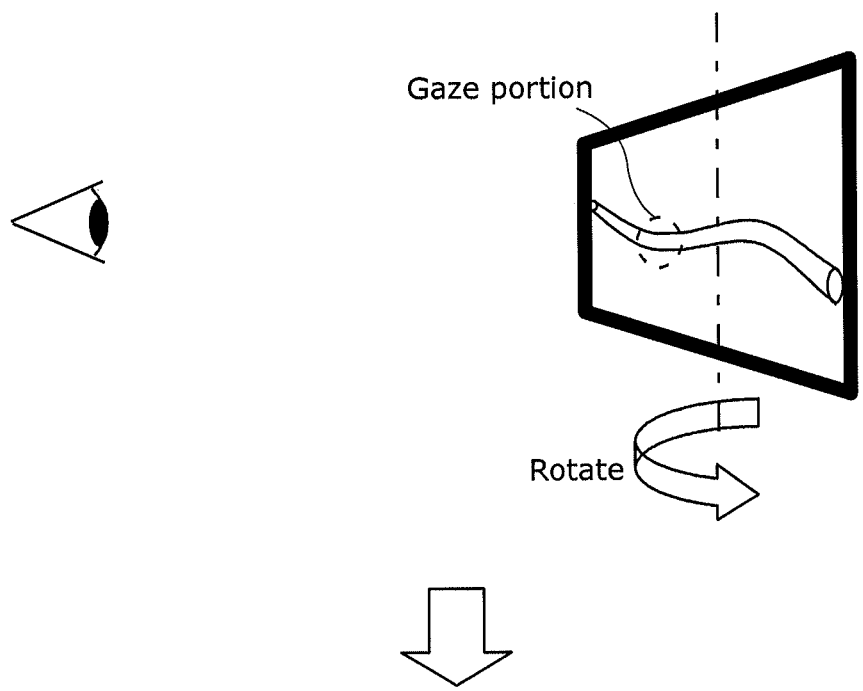
(b)
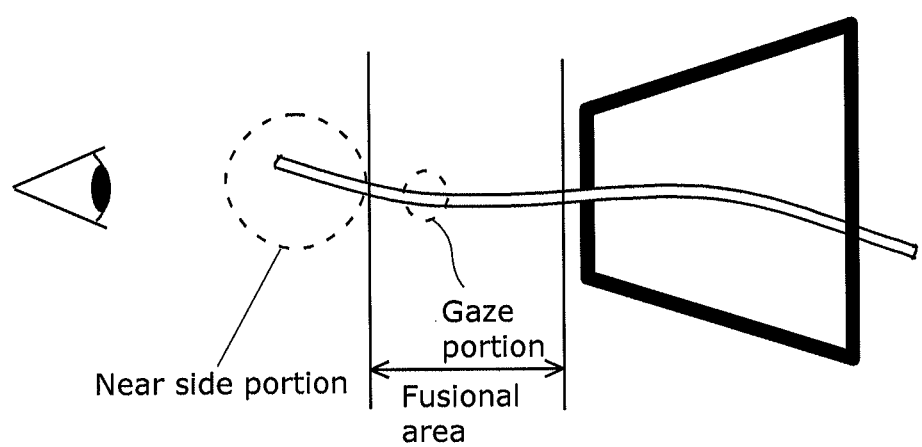

FIG. 5
(a)
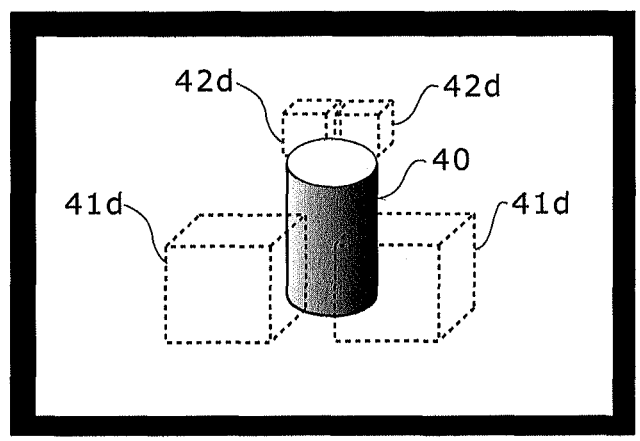
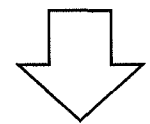
(b)
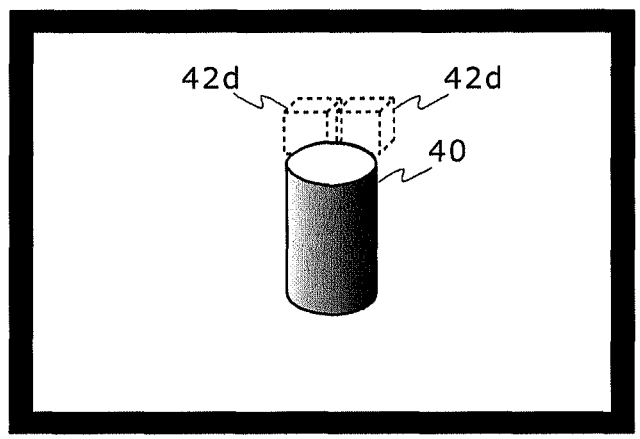

| Coordinate | Display color |
|---|---|
| (21, 19, 187) | R:121 G:41 B:64 |
| (22, 18, 173) | R:123 G:48 B:64 |
| (20, 19, 180) | R:124 G:52 B:62 |
| ⋮ | ⋮ |

101a

Cameras

Measurement electrodes

FIG. 12

| Depth of gaze point | Near side fusion limit | Far side fusion limit |
|---|---|---|
| to 200 mm | Gaze point -10 mm | Gaze point +10 mm |
| 201 mm to 300 mm | Gaze point -15 mm | Gaze point +15 mm |
| 301 mm to 500 mm | Gaze point -20 mm | Gaze point +20 mm |
| ⋮ | ⋮ | ⋮ |

108a

FIG. 18
(a)
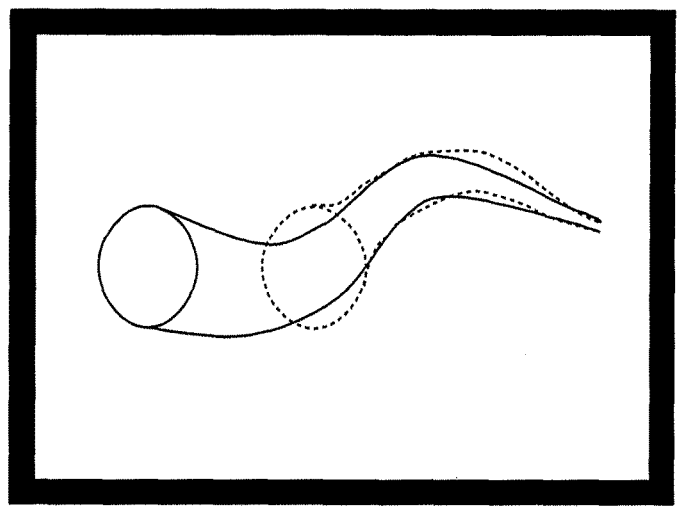
(b)

| Coordinate | Display color | Blood vessel ID | Branch number |
|---|---|---|---|
| (21, 19, 187) | R:121 G:41 B:64 | A01 | 11 |
| (22, 18, 173) | R:123 G:48 B:64 | A01 | 111 |
| (20, 19, 180) | R:124 G:52 B:62 | A02 | 12 |
| ⋮ | ⋮ | ⋮ | ⋮ |

First score translation table

| Fusional status | Score |
|---|---|
| Double vision (near side) | -1500 |
| Fusion | 0 |
| Double vision (far side) | -600 |

FIG. 27B

Second score translation table

| Spatial distance | Score |
|---|---|
| 0 - 5 | 2000 |
| 6 - 10 | 1500 |
| 10 - 20 | 1300 |
| ⋮ | ⋮ |

Third score translation table

| Branch distance | Score |
|---|---|
| 0 | 1300 |
| 1 | 1000 |
| 2 - 4 | 500 |
| ⋮ | ⋮ |

FIG. 29

| Blood vessel importance | Area code | Correction process |
|---|---|---|
| to -1001 | 1 | Hiding |
| -1000 to -501 | 2 | Semi-transparentizing |
| -500 to -301 | 3 | Blurring 1 |
| -300 to -101 | 4 | Blurring 2 |
| -100 to -1 | 5 | Blurring 3 |
| 0 or greater | 6 | No correction |

First score translation table

| Fusional status | Score |
|---|---|
| Double vision (near side) | -1500 |
| Fusion | 0 |
| Double vision (far side) | -600 |

FIG. 34B

Second score translation table

| Spatial distance | Score |
|---|---|
| 0 - 5 | 2000 |
| 6 - 10 | 1500 |
| 10 - 20 | 1300 |
| ⋮ | ⋮ |

FIG. 34C

Third score translation table

| Branch distance | Score |
|---|---|
| 0 | 800 |
| 1 | 500 |
| 2 - 4 | 100 |
| ⋮ | ⋮ |

FIG. 34D

Fourth score translation table

| Branch distance | Score |
|---|---|
| 0 | 1300 |
| 1 | 1000 |
| 2 - 4 | 800 |
| ⋮ | ⋮ |

FIG. 34E

Fifth score translation table

| Branch distance | Score |
|---|---|
| 0 | 500 |
| 1 | 100 |
| 2 - 4 | 0 |
| ⋮ | ⋮ |

THREE-DIMENSIONAL DISPLAY DEVICE, THREE-DIMENSIONAL IMAGE PROCESSING DEVICE, AND THREE-DIMENSIONAL DISPLAY METHOD

CROSS REFERENCE TO RELATED APPLICATIONS

This is a continuation application of PCT International Application No. PCT/JP2013/005666 filed on Sep. 25, 2013, designating the United States of America, which is based on and claims priority of Japanese Patent Application No. 2012-224565 filed on Oct. 9, 2012. The entire disclosures of the above-identified applications, including the specifications, drawings and claims are incorporated herein by reference in their entirety

FIELD

One or more exemplary embodiments disclosed herein relate generally to technology for displaying or processing a three-dimensional medical image.

BACKGROUND

Changing a viewpoint (e.g., rotation or zoom) of a three-dimensional, image (e.g., a left-eye image and a right-eye image) changes a positional relationship in the depth direction between a plurality of objects included in the three-dimensional image or between portions of an object. As a result, for example, an object located on a far side is hidden by an object on a near side, reducing the visibility of the three-dimensional image.

In response, Patent Literature (PTL) 1 discloses a method for adjusting transparency of an object included in a three-dimensional image in accordance with a depth of the object. This can display an object located on a far side through an object located on a near side.

Moreover, PTL 2 discloses a method for maintaining stereoscopic effects by adjusting an amount of a disparity between a left-eye image and a right-eye image in accordance with a focal length upon zooming a three-dimensional image.

CITATION LIST

Patent Literature

[PTL 1] Japanese Unexamined Patent Application Publication No. 2001-84409
[PTL 2] Japanese Unexamined Patent Application Publication No. 2011-248693

SUMMARY

Technical Problem

In the above conventional methods, however, the visibility of the three-dimensional image may decrease depending on a state of a viewer or a three-dimensional image.

Thus, one non-limiting and exemplary embodiment provides a three-dimensional display device which can improve visibility of a three-dimensional image, adapting to a state of a viewer or the three-dimensional image.

Solution to Problem

In one general aspect, the techniques disclosed here feature a three-dimensional display device for displaying a three-dimensional image, including: a gaze point obtaining unit configured to obtain a position of a gaze point of a viewer; a fusional area determination unit configured to determine a fusional area where binocular fusion is allowed, based on the obtained position of the gaze point; a correction unit configured to correct the three-dimensional image so as to suppress display of an object which is included in the three-dimensional image outside the fusional area; and a display unit configured to display the corrected three-dimensional image.

These general and specific aspects may be implemented using a system, a method, an integrated circuit, a computer program, or a computer-readable recording medium such as a CD-ROM, or any combination of systems, methods, integrated circuits, computer programs, or computer-readable recording media such as CD-ROM.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

According to a three-dimensional display device of one or more exemplary embodiments or features disclosed herein, visibility of a three-dimensional image can be improved, adapting to a state of a viewer or the three-dimensional image.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 1 shows schematic views illustrating examples of an image of a blood vessel displayed three-dimensionally.

FIG. 5 shows diagrams illustrating examples of the three-dimensional image displayed by the three-dimensional display device according to the embodiment 1.

FIG. 12 is a diagram showing an example of fusional area information in the embodiment 2.

FIG. 18 shows diagrams illustrating an example of a three-dimensional image displayed by the three-dimensional display device according to the embodiment 2.

FIG. 27A is a diagram showing an example of a score translation table in the embodiment 3.

FIG. 27B is a diagram showing an example of the score translation table in the embodiment 3.

FIG. 29 is a diagram showing an example of a segmentation table in the embodiment 3.

FIG. 34A is a diagram showing an example of a score translation table in the embodiment 4.

FIG. 34B is a diagram showing an example of the score translation table in the embodiment 4.

FIG. 34C is a diagram showing an example of the score translation table in the embodiment 4.

FIG. 34D is a diagram showing an example of the score translation table in the embodiment 4.

FIG. 34E is a diagram showing an example of the score translation table in the embodiment 4.

Figure 2:
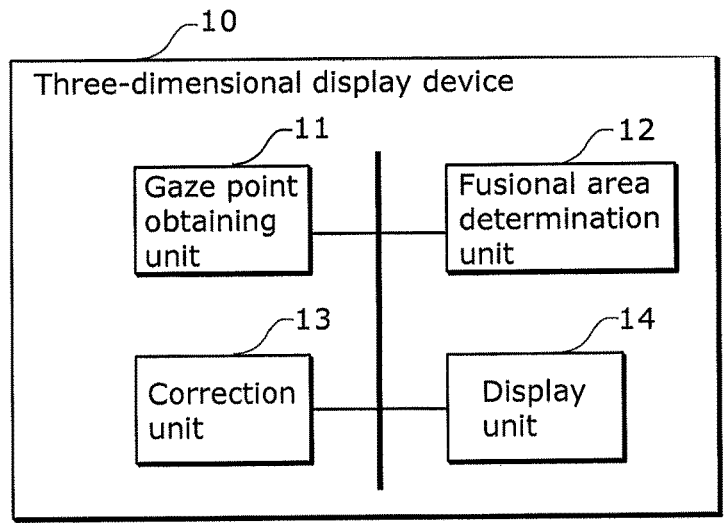
FIG. 2 is a block diagram of a functional configuration of a three-dimensional display device according to an embodiment 1.

DESCRIPTION OF EMBODIMENTS (Underlying Knowledge Forming Basis of the Present Disclosure)

When a displayed three-dimensional image changes or a position of a point of gaze of a viewer changes, a relationship changes between an object and a portion of the object (hereinafter, these are collectively referred to as a "near side portion") which are displayed projecting toward a side closer to the viewer than an object and a portion of the object which a viewer is gazing (hereinafter, these are collectively referred to as a "gaze portion") and an object and a portion of the object displayed receding into a side (hereinafter, these are collectively referred to as a "far side portion") farther away from the viewer than the gaze portion is. At this time, visibility of the gaze portion decreases due to positions or patterns of the near side portion and the far side portion. For example, when the near side portion overlaps with the gaze portion in the depth direction, the gaze portion ends up being hidden by the near side portion.

In response, according to the method disclosed in PTL 1, visibility of a gaze portion can be improved by adjusting transparency of a near side portion. The method of PTL 1, however, requires a viewer to manually adjust transparency of an object or a portion of the object in a three-dimensional image. In other words, the method of PTL 1 requires a viewer to manually adjust the transparency of the object or the portion thereof every time a state of the viewer or the three-dimensional image changes.

Moreover, in the method of PTL 2, an amount of a disparity can be automatically adjusted in accordance with a focal length whereas visibility of a gaze portion cannot be improved.

Herein, an example of a state where the gaze portion is hidden by the near side portion in the three-dimensional image will be described in detail, with reference to a three-dimensional image of a blood vessel (hereinafter, simply referred to as an "image of a blood vessel").

FIG. 1 shows examples of an image of a blood vessel displayed three-dimensionally.

In (a) of FIG. 1, a blood vessel is displayed along a display screen. As the image of the blood vessel displayed in (a) of FIG. 1 is rotated, the image of the blood vessel is displayed, for example, as shown in (b) of FIG. 1. Here, the image of the blood vessel is rotated about, as the rotation axis, an axis of the vertical direction passing through the center of the screen.

The blood vessel displayed in (a) of FIG. 1 has two curved portions on the left and right sides of the screen. A viewer performs an operation for rotating the image of the blood vessel to see the curved portion on the left side from a different angle. In the example of FIG. 1, the image is rotated such that an object on the left side of the screen moves to the front of the screen and an object on the right side of the screen moves behind the screen.

At this time, as (b) of FIG. 1 shows, the curved portion (the gaze portion) which the viewer desires to view is displayed at a three-dimensional position closer to the viewer than the screen is. However, the portion displayed on the left of the gaze portion in (a) of FIG. 1 is displayed even closer to the viewer than the gaze portion is. As a result, the portion (the near side portion), which is displayed closer to the viewer than the gaze portion is, ends up hiding the gaze portion.

Furthermore, the blood vessel disposed along with the depth direction causes a large difference in depth between an end portion of the blood vessel on the front side and an end portion on the far side. This causes the object other than portions thereof near the gaze portion to appear double to the viewer.

The depth of a three-dimensional image is represented by a disparity between a left-eye image and a right-eye image. Thus, a three-dimensional image having portions which are significantly different in depth includes areas which are significantly different in disparity.

When seeing a three-dimensional image, a person adjusts an angle between the left and right eyes (an angle of convergence) to the disparity. As a result, the person can overlap two images obtained from the left eye and the right eye to obtain an image, thereby viewing an object in a stereoscopic manner. Overlapping two images obtained from both eyes to obtain an image as such is referred to as binocular fusion or, simply, fusion.

For example, for a three-dimensional image having two objects which are significantly different from each other in disparity, if an angle of convergence is adjusted to the disparity of one of the two objects, the angle of convergence does not conform to the disparity of the other of the two objects. As a result, the object that has the disparity to which the angle of convergence does not conform ends up causing double vision (diplopia). In other words, double vision outside the fusional area is undesirably produced.

In (a) of FIG. 1, there are small changes in depth between the gaze portion and the other portions. Thus, differences in disparity in the three-dimensional image are also small. Therefore, adjusting the angle of convergence so as to conform to the disparity of the gaze portion prevents double vision from occurring.

On the other hand, in (b) of FIG. 1, a three-dimensional position in the depth direction at which the blood vessel is displayed is significantly different depending on a portion of the blood vessel. Thus, for example, a disparity at a near side portion is greater than a disparity at the gaze portion, wherein, it is known that if the angle of convergence is adjusted conforming to the disparity at the gaze portion, a disparity (i.e., depth) where the fusion is allowed by the angle of convergence has a certain width rather than being limited to the disparity (i.e., depth) at the gaze portion.

An area where binocular fusion is allowed will be referred to as fusional area (fusional limits of depth perception). A fusional area has a viewing angle of a few minutes at the center of a field of view, which is extremely narrower than that at the periphery (Panum's fusional area). Moreover, the fusional area reduces as the gaze portion is located on a side closer to the viewer in the depth direction, and increases as the gaze portion is located on a side farther away from the viewer. Thus, double vision is more likely to be caused as closer to the viewer the gaze portion is located.

Thus, a three-dimensional display device according to an exemplary embodiment disclosed herein is a three-dimensional display device for displaying a three-dimensional image, including: a gaze point obtaining unit configured to obtain a position of a gaze point of a viewer; a fusional area determination unit configured to determine a fusional area where binocular fusion is allowed, based on the obtained position of the gaze point; a correction unit configured to correct the three-dimensional image so as to suppress display of an object which is included in the three-dimensional image outside the fusional area; and a display unit configured to display the corrected three-dimensional image.

According to the above configuration, the three-dimensional image can be corrected so as to suppress display of objects that are included in the three-dimensional image outside the fusional area. This can therefore suppress visual effects which are caused by double vision produced outside the fusional area. As a result, the visibility of an object which the viewer is gazing in the three-dimensional image can be improved.

Furthermore, according to the above configuration, the three-dimensional image can be corrected using a fusional area that is automatically determined in accordance with a position of a point of gaze. Thus, the viewer is not required to designate an object the display of which is to be suppressed, thereby improving viewer convenience as well.

For example, the correction unit may correct the three-dimensional image by removing an object which is included in the three-dimensional image and located on a side closer to the viewer than the fusional area is.

According to the above configuration, objects located on the nearer side than the fusional area can be removed from the three-dimensional image. Thus, double vision in an area on the nearer side than the fusional area can be prevented from occurring. Furthermore, an object which the viewer is gazing can be prevented from being hidden by another object. As a result, further improvement in the visibility of the object which the viewer is gazing in the three-dimensional image is possible.

For example, the correction unit may correct the three-dimensional image by blurring an object which is included in the three-dimensional image and located on a side farther away from the viewer than the fusional area is.

According to the above configuration, an object located on the farther side than the fusional area can be blurred. This can therefore suppress visual effects which are caused by double vision produced on the farther side than the fusional area.

For example, the three-dimensional display device may further include a viewpoint changing unit configured to change a viewpoint of the three-dimensional image so that a display position of an object which is included in the three-dimensional image and located at the position of the gaze point does not change in a depth direction, wherein the correction unit may correct the three-dimensional image the viewpoint of which has been changed.

According to the above configuration, the viewpoint of the three-dimensional image can be changed so that the display position of the object displayed at the position of point of gaze does not change in the depth direction. Thus, the viewer can continue gazing at the same object without changing the angle of convergence. Thus, load imposed on the viewer can be reduced.

For example, changing the viewpoint may be a process of rotating the three-dimensional image about the position of the gaze point.

According to the above configuration, the rotation process about the position of the point of gaze can be performed on the three-dimensional image. As a result, the viewpoint of the three-dimensional image can be changed so that the display position of the object displayed at the position of point of gaze does not change.

For example, the three-dimensional display device may further include a fusional area information storage unit configured to store fusional area information which indicates positions of a plurality of gaze points in a depth direction of the three-dimensional image and a plurality of fusional areas corresponding to the positions of the plurality of gaze points in the depth direction, wherein the fusional area determination unit may refer to the fusional area information to determine the fusional area that corresponds to the obtained position of the gaze point.

According to the above configuration, referring to the fusional area information facilitates determination of a fusional area that corresponds to the obtained position of the point of gaze.

For example, the three-dimensional image may include a plurality of blood vessel objects representing a plurality of blood vessels, the three-dimensional display device further including: a blood vessel connection information obtaining unit configured to obtain connection information indicating connectivity of a blood vessel object located at the gaze point to each of the blood vessel objects included in the three-dimensional image; and a blood vessel importance calculation unit configured to calculate importance of each of the blood vessel objects included in the three-dimensional image, based on the fusional area and the connection information, wherein the correction unit may correct the three-dimensional image so that display of a blood vessel object the importance of which is lower is suppressed to a greater extent.

According to the above configuration, the three-dimensional image can be corrected so that display of a blood vessel object the importance of which is lower is suppressed to a greater extent, the importance being calculated based on the fusional area and the connection information. Thus, suppression of display of a blood vessel object in accordance with the blood vessel object located at the point of gaze is possible.

For example, the blood vessel importance calculation unit may calculate, each of the blood vessel objects, the importance of the blood vessel object so that the blood vessel object, if included in the fusional area, is of higher importance than if the blood vessel object is not included in the fusional area.

According to the above configuration, importance of a blood vessel object can be calculated so that the blood vessel object, if included in the fusional area, is of higher importance than if the blood vessel object is not included in the fusional area. Thus, suppression of blood vessel objects that not included in the fusional area is possible.

For example, the blood vessel importance calculation unit may calculate, for each of the blood vessel object, the importance of the blood vessel object so that the blood vessel object having a less number of blood vessel branches to the blood vessel object located at the gaze point is of higher importance.

According to the above configuration, importance of a blood vessel object can be calculated so that the blood vessel object having a less number of blood vessel branches to the blood vessel object located at the point of gaze is of higher importance. Thus, display of blood vessel objects which are connected to the blood vessel object located at the point of gaze via a large number of branches can be suppressed, thereby improving the visibility of the blood vessel object located at the point of gaze.

For example, the blood vessel importance calculation unit may calculate, for each of the blood vessel objects, the importance of the blood vessel objects so that the blood vessel object having a smaller spatial distance to the blood vessel object located at the gaze point is of higher importance.

According to the above configuration, importance of a blood vessel object can be calculated so that the blood vessel object having a smaller spatial distance to the blood vessel object located at the point of gaze is of higher importance. Thus, display of blood vessel objects that have great spatial distances to the object located at the point of gaze can be suppressed, thereby improving the visibility of the blood vessel object located at the point of gaze.

For example, the three-dimensional image may include a plurality of blood vessel objects representing a plurality of blood vessels, and an instrument object representing a medical instrument which is advanced through at least one of the blood vessel objects, the three-dimensional display device further including an identification unit configured to identify, among the plurality of blood vessel objects, a blood vessel object through which the instrument object has already passed or a blood vessel object through which the instrument object does not pass, wherein the correction unit may correct the three-dimensional image so as to suppress display of a blood vessel object which is located outside the fusional area and through which the instrument object has already passed or display of a blood vessel object which is located outside the fusional area and through which the instrument object does not pass.

According to the above configuration, the three-dimensional image can be corrected so as to suppress display of a blood vessel object through which the instrument object has already passed or display of a blood vessel object through which the instrument object does not pass. Thus, display of a blood vessel object through which the instrument object is likely to be advanced can be prioritized, thereby displaying a useful three-dimensional image.

Moreover, a three-dimensional image processing device according to an exemplary embodiment disclosed herein is a three-dimensional image processing device for processing a three-dimensional image including a plurality of blood vessel objects representing a plurality of blood vessels, and an instrument object representing a medical instrument which is advanced through at least one of the blood vessel objects, the three-dimensional image processing device including: a gaze point obtaining unit configured to obtain a position of a gaze point of a viewer; a fusional area determination unit configured to determine a fusional area where binocular fusion is allowed, based on the obtained position of the gaze point; an identification unit configured to identify, among the plurality of blood vessel objects, a blood vessel object through which the instrument object has already passed or a blood vessel object through which the instrument object does not pass; and a correction unit configured to correct the three-dimensional image so as to suppress display of a blood vessel object which is located outside the fusional area and through which the instrument object has already passed or display of a blood vessel object which is located outside the fusional area and through which the instrument object does not pass.

These general and specific aspects may be implemented using a system, a method, an integrated circuit, a computer program, or a computer-readable recording medium such as a CD-ROM, or any combination of systems, methods, integrated circuits, computer programs, or computer-readable recording media such as CD-ROM.

Hereinafter, certain exemplary embodiments will be described in greater detail, with reference to the accompanying drawings.

It should be noted that the non-limiting embodiments described below are general and specific illustration. Values, shapes, materials, components, disposition or a form of connection between the components, steps, and the order of the steps described in the following embodiments are merely illustrative, and are not intended to limit the appended claims. Moreover, among components of the below embodiments, components not set forth in the independent claims indicating the top level concept of the present disclosure will be described as optional components.

In the following, unnecessarily detailed description may be omitted. For example, detailed description of well-known matters or description previously set forth with respect to components that are substantially the same may be omitted. This is to avoid unnecessarily redundancy in the description below and for facilitating an understanding by those skilled in the art.

Embodiment 1

<Configuration>

FIG. 2 is a block diagram of a functional configuration of a three-dimensional display device 10 according to an embodiment 1. The three-dimensional display device 10 displays a three-dimensional image. In other words, the three-dimensional display device 10 displays an image in a stereoscopic manner. Specifically, the three-dimensional display device 10 displays a three-dimensional image by a glasses based stereoscopic display method. The glasses based stereoscopic display method is for displaying a left-eye image and a right-eye image, which have the disparity therebetween, to a viewer wearing glasses (such as LCD shutter glasses and polarized glasses). Also for example, the three-dimensional display device 10 may display a three-dimensional image by autostereoscopy. The autostereoscopy is a stereoscopic display method without the use of glasses (such as parallax barrier and Lenticular lens technologies).

As FIG. 2 shows, the three-dimensional display device 10 includes a gaze point obtaining unit 11, a fusional area determination unit 12, a correction unit 13, and a display unit 14.

The gaze point obtaining unit 11 obtains a position of a point of gaze of a viewer. Specifically, the gaze point obtaining unit 11, for example, detects a three-dimensional position of a point of gaze, based on electrooculograms of a viewer or an image of the eyes. It should be noted that the gaze point obtaining unit 11 may not detect a position of the point of gaze. For example, the gaze point obtaining unit 11 may obtain a position of the point of gaze by obtaining information indicative of the position of the point of gaze from a sensor or the like provided external to the three-dimensional display device 10.

The fusional area determination unit 12 determines a fusional area where binocular fusion is allowed, based on the obtained position of the point of gaze. Specifically, the fusional area determination unit 12 determines a fusional area corresponding to the obtained position of the point of gaze by, for example, referring to fusional area information indicating positions of a plurality of points of gaze in the depth direction and a plurality of fusional areas corresponding to the respective positions of the plurality of points of gaze in the depth direction. Also for example, the fusional area determination unit 12 may determine a fusional area by a mathematical formula for calculating the fusional area from the position of the point of gaze.

The correction unit 13 corrects the three-dimensional image so as to suppress display of an object that is included in the three-dimensional image outside the fusional area. Suppressing the display of an object means lowering a display level of the object. For example, the display of the object can be controlled by increasing the transparency of the object or reducing the definition of the object. It should be noted that controlling the display of an object includes hiding (transparentizing) the object.

Specifically, the correction unit 13 corrects the three-dimensional image by, for example, removing an object which is included in the three-dimensional image and located on a side closer to the viewer (hereinafter, referred to as a nearer side) than the fusional area is. Also for example, the correction unit 13 may correct the three-dimensional image by blurring an object which is included in the three-dimensional image and located on a side farther away from the viewer (hereinafter, referred to as a farther side) than the fusional area is.

More specifically, the correction unit 13 renders a left-eye image and a right-eye image, using only three-dimensional models located within an area corresponding to the fusional area in a virtual three-dimensional space where, for example, a plurality of three-dimensional models indicating a plurality of objects included in the three-dimensional image are disposed. Also for example, the correction unit 13 may increase transparency of three-dimensional models outside the area corresponding to the fusional area, and then render a left-eye image and a right-eye image.

The display unit 14 displays the corrected three-dimensional image. Specifically, the display unit 14, for example, alternately displays the left-eye image and the right-eye image on the screen, thereby displaying the corrected three-dimensional image. Also for example, the display unit 14, for example, displays the left-eye image using, among a plurality of pixels arrayed in matrix on the screen, left pixels which can be seen by the left eye, and displays the right-eye image using right pixels which can be seen by the right eye.

It should be noted that the display unit 14 may not have a screen. In this case, the display unit 14 may display the three-dimensional image via a display device external to the three-dimensional display device 10.

Next, various operations of the three-dimensional display device 10 configured as set forth above will be described.

<Operation>

Figure 3:
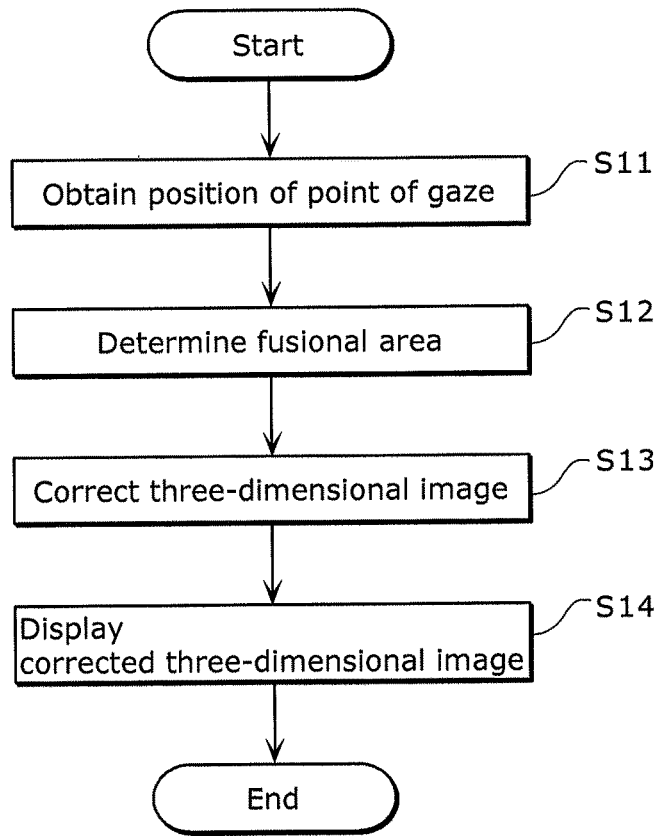
FIG. 3 is a flowchart illustrating processing operation of the three-dimensional display device according to the embodiment 1.

FIG. 3 is a flowchart illustrating processing operation of the three-dimensional display device 10 according to the embodiment 1.

First, the gaze point obtaining unit 11 obtains a position of a point of gaze of the viewer (S11). Subsequently, the fusional area determination unit 12 determines a fusional area, based on the position of the point of gaze (S12). Then, the correction unit 13 corrects the three-dimensional image so as to suppress display of an object that is included in the three-dimensional image outside the fusional area (S13). Last, the display unit 14 displays the corrected three-dimensional image (S14).

The processing operation of the three-dimensional display device 10 will be described in more detail, with reference to FIGS. 4 and 5.

Figure 4:
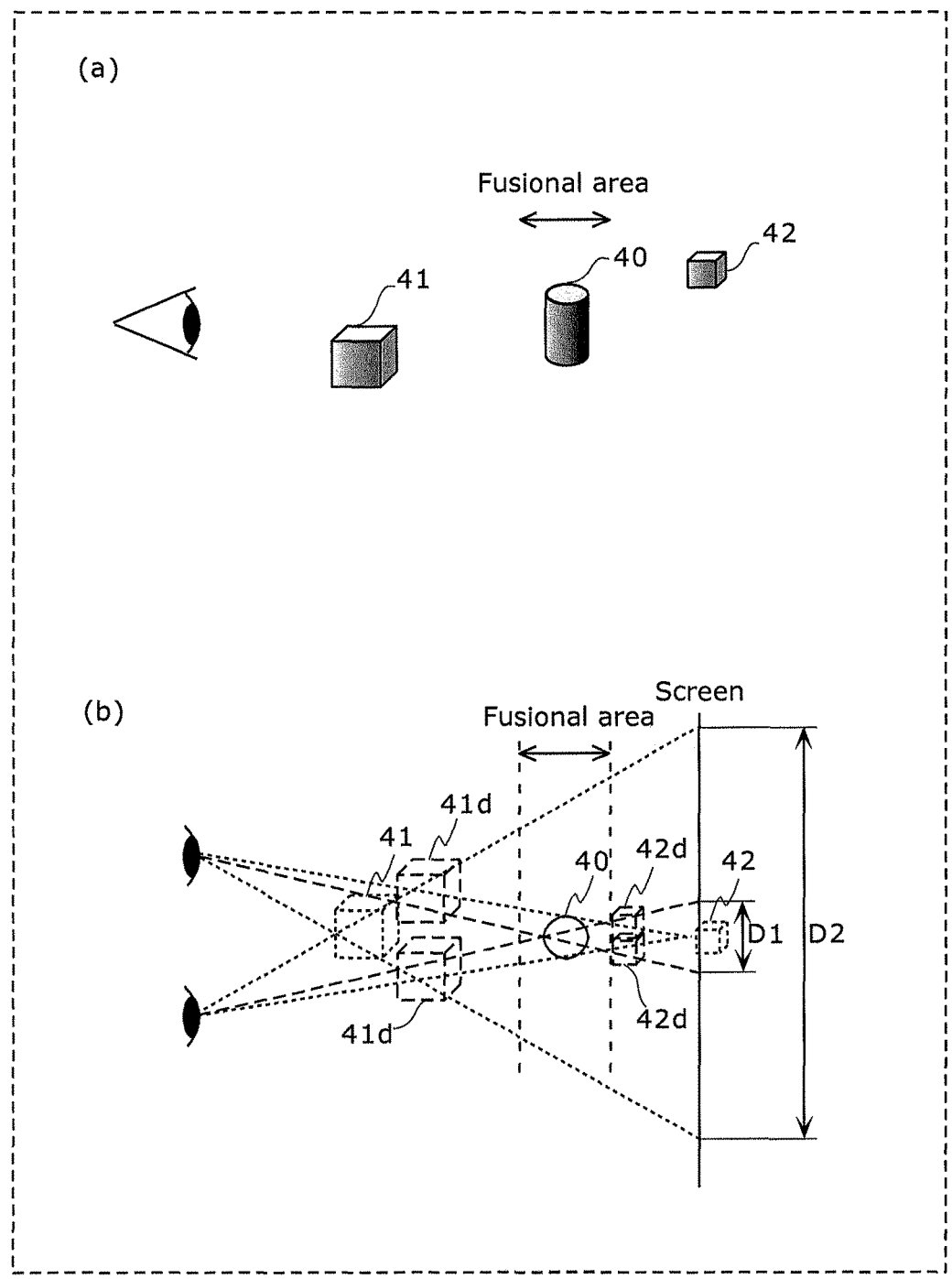
FIG. 4 shows schematic views for illustrating processing operation of the three-dimensional display device according to the embodiment 1.

FIG. 4 shows schematic views for illustrating the processing operation of the three-dimensional display device 10 according to the embodiment 1. Specifically, (a) of FIG. 4 is a diagram showing a positional relationship between objects 40, 41, and 42 included in the three-dimensional image. Part (b) of FIG. 4 is an explanatory diagram of double vision.

FIG. 5 shows diagrams illustrating examples of the three-dimensional image which is displayed by the three-dimensional display device 10 according to the embodiment 1. Specifically, (a) of FIG. 5 shows an uncorrected three-dimensional image, and (b) of FIG. 5 shows a corrected three-dimensional image.

As illustrated in (a) of FIG. 4, the object 41 is displayed on a nearer side than the object 40, and the object 42 is displayed on a farther side than the object 40. As (b) of FIG. 4 illustrates, a disparity D1 of the object 40 is smaller than a disparity D2 of the object 41 and greater than a disparity of the object 42.

Here, suppose that the position of the point of gaze is a display position of the object 40, the fusional area is a neighboring area of the object 40. At this time, the object 41 is located outside (the nearer side than) the fusional area. In other words, the angle of convergence of the viewer does not conform to the disparity of the object 41. Thus, double vision 41d is caused. The object 42 is also located outside (the farther side than) the fusional area. In other words, the angle of convergence of the viewer does not conform to the disparity of the object 42. Thus, double vision 42d is caused. In other words, the viewer perceives the three-dimensional image as shown in (a) of FIG. 5.

In this case, particularly, the double vision 41d on the nearer side than the object 40, which is a gaze object, reduces the visibility of the object 40. Thus, for example, by removing the object 41 from the three-dimensional image, the correction unit 13 corrects the three-dimensional image so as to suppress the display of the object 41. As a result, as (b) of FIG. 5 shows, the double vision 41d on the nearer side than the object 40 is removed, improving the visibility of the object 40.

Moreover, for example, if the objects 40 and 42 have a similar pattern, the double vision 42d on the farther side than the object 40 also reduces the visibility of the object 40. Thus, for example, by blurring the object 42 in the three-dimensional image, the correction unit 13 corrects the three-dimensional image so as to suppress the display of the object 42. As a result, the object 40 is highlighted greater than the double vision 42d, improving the visibility of the object 40.

<Effects>

As described above, according to the present embodiment, the three-dimensional display device 10 can correct the three-dimensional image so as to suppress display of objects that are included in the three-dimensional image outside the fusional area. Thus, the three-dimensional display device 10 can suppress visual effects which are caused by double vision produced outside the fusional area. As a result, the three-dimensional display device 10 can improve the visibility of an object which the viewer is gazing in the three-dimensional image.

Furthermore, according to the present embodiment, the three-dimensional display device 10 can correct the three-dimensional image, using a fusional area that is automatically determined in accordance with a position of a point of gaze. Thus, the viewer is not required to designate an object the display of which is to be suppressed. The three-dimensional display device 10 can thus improve viewer convenience as well.

Embodiment 2

Next, an embodiment 2 will be described in detail. In the present embodiment, description will be given where a viewpoint of a displayed three-dimensional image is changed.

<Configuration>

Figure 6:
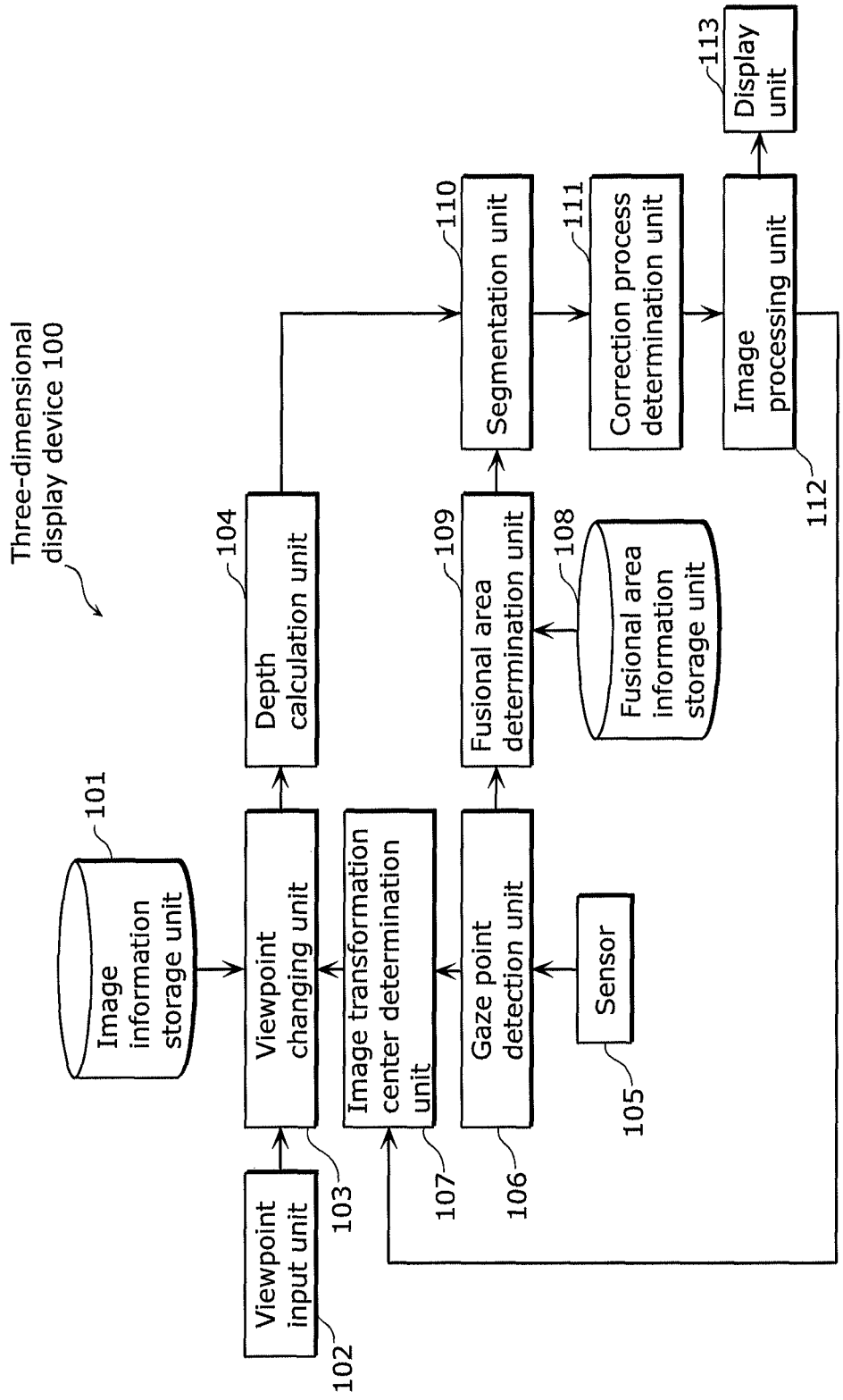
FIG. 6 is a block diagram of a functional configuration of a three-dimensional display device according to an embodiment 2.

FIG. 6 is a block diagram of a functional configuration of a three-dimensional display device 100 according to the embodiment 2.

The three-dimensional display device 100 includes an image information storage unit 101, a viewpoint input unit 102, a viewpoint changing unit 103, a depth calculation unit 104, a sensor 105, a gaze point detection unit 106, an image transformation center determination unit 107, a fusional area information storage unit 108, a fusional area determination unit 109, a segmentation unit 110, a correction process determination unit 111, an image processing unit 112, and a display unit 113.

The image information storage unit 101 is, for example, a hard disk drive or a semiconductor memory. The image information storage unit 101 stores image information 101a on a three-dimensional image which is displayed. Specifically, the image information storage unit 101, for example, stores three-dimensional models of objects included in the three-dimensional image, as the image information 101a.

Figures 7, 8A:
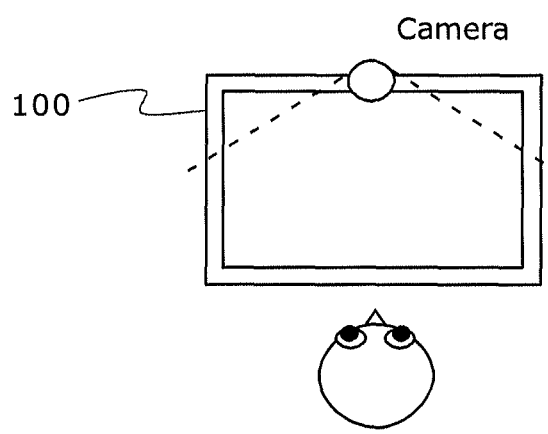
FIG. 7 is a diagram showing an example of image information in the embodiment 2.
FIG. 8A is a schematic view illustrating an example of a sensor according to the embodiment 2.

In the present embodiment, the image information storage unit 101 stores information on blood vessel objects, each representing a blood vessel, as the image information 101a. The image information 101a includes coordinates and display colors of points on a blood vessel object, for example, as shown in FIG. 7.

The viewpoint input unit 102 is an interface which inputs operation for changing a viewpoint (e.g., rotation or zoom) of a display image. Examples of the viewpoint input unit 102 include a mouse, a remote controller, and a gesture detection device. Herein, viewpoint change refers to a process of changing a viewpoint and a viewing direction (a position and a direction of a virtual camera) with respect to an object included in a three-dimensional image. For example, changing a viewpoint of a three-dimensional image such that the viewpoint approaches an object enlarges the object.

Using the image information 101a stored in the image information storage unit 101, the viewpoint changing unit 103 changes a viewpoint of the three-dimensional image, based on the operation for changing the viewpoint received by the viewpoint input unit 102. At this time, the viewpoint changing unit 103 changes the viewpoint of the three-dimensional image so that a display position of an object that is included in the three-dimensional image and displayed at a position of the point of gaze does not change in the depth direction.

The viewpoint change, is, for example, a process of rotating the three-dimensional image about the position of the point of gaze. Specifically, the viewpoint changing unit 103 changes the viewpoint of the three-dimensional image, using a central position, which is determined by the image transformation center determination unit 107, as a central position about which the viewpoint is to be changed. For example, the viewpoint changing unit 103 rotates the three-dimensional image about an axis in the vertical direction passing through the central position determined by the image transformation center determination unit 107.

The depth calculation unit 104 calculates a depth of the object included in the three-dimensional image which has undergone the viewpoint change by the viewpoint changing unit 103.

Figure 8B:
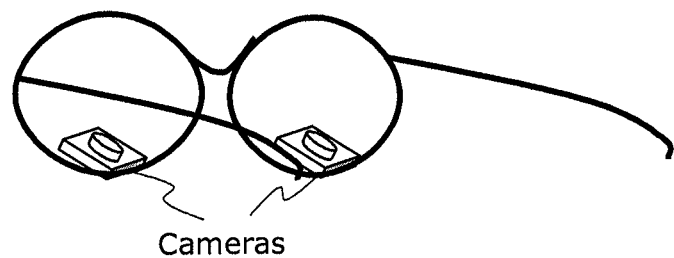
FIG. 8B is a schematic view illustrating another example of the sensor according to the embodiment 2.
Figure 9:
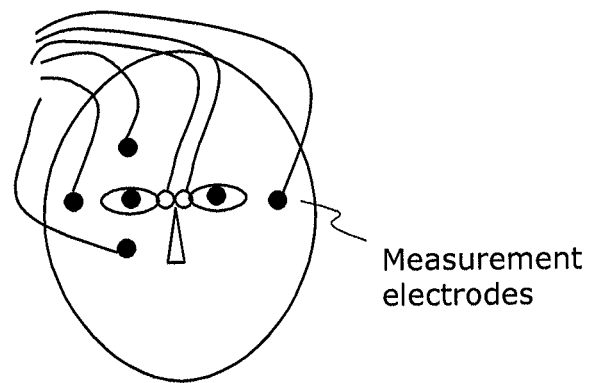
FIG. 9 is a schematic view illustrating another example of the sensor according to the embodiment 2.
Figure 10:
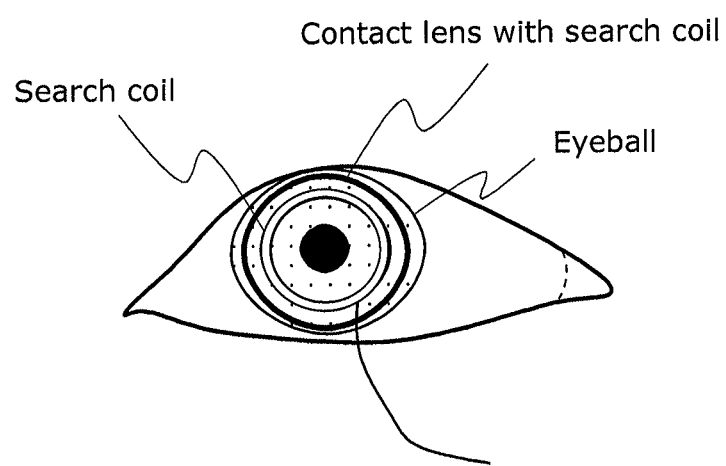
FIG. 10 is a schematic view illustrating another example of the sensor according to the embodiment 2.

The sensor 105 senses eye movement of a viewer viewing the three-dimensional image. The sensor 105 is a visible light camera or an infrared camera which captures images of the viewer's eyes, for example, as shown in FIG. 8A or 8B. Also for example, the sensor 105 may be electrooculogram measuring means or myopotential measuring means which records changes in potential associated with the eye movement from electrodes in contact with a skin as illustrated in FIG. 9. Also for example, the sensor 105 may be a search coil which records changes in potential associated with the eye movement and movement of the iris of the eye or movement of the lens, from a coil in contact with the surface of an eyeball as illustrated in FIG. 10.

Figure 11:
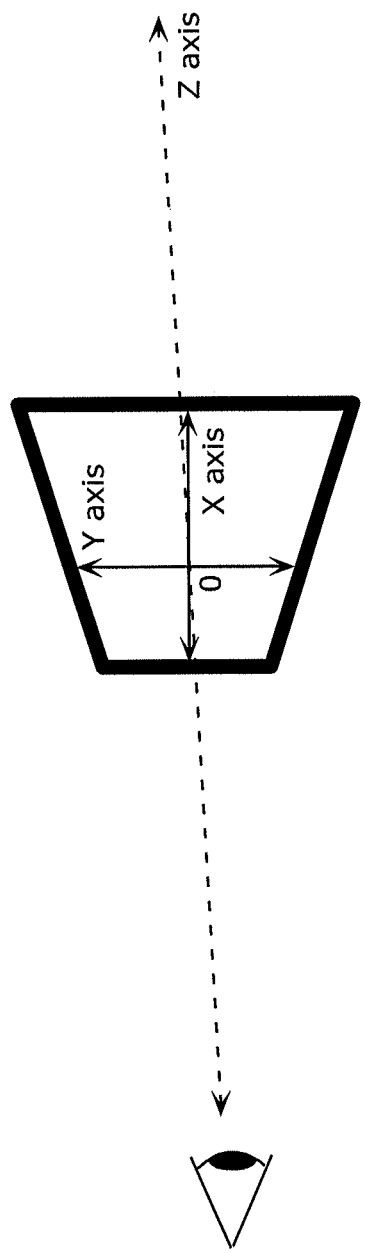
FIG. 11 is a schematic view illustrating an example of a coordinate system in the embodiment 2.

The gaze point detection unit 106 calculates a position (a three-dimensional position) of a point of gaze of the viewer, using information on the viewer's eye movement sensed by the sensor 105. At this time, a coordinate system for representing the three-dimensional position is a three-dimensional display coordinate system, for example, as shown in FIG. 11. In the three-dimensional display coordinate system of FIG. 11, origin is at the center of a screen surface, the horizontal direction on a screen plane is the X axis, the vertical direction on the screen plane is the Y axis, and a direction perpendicular to the screen plane is the Z axis.

In other words, in the present embodiment, the position of the point of gaze of the viewer is obtained, using the sensor 105 and the gaze point detection unit 106. It should be noted that the sensor 105 and the gaze point detection unit 106 may not be included in the three-dimensional display device 100. In this case, the three-dimensional display device 100 may obtain the position of the point of gaze of the viewer which is detected by the sensor 105 and the gaze point detection unit 106.

The image transformation center determination unit 107 determines the position of the point of gaze of the viewer detected by the gaze point detection unit 106 as a central position about which the viewpoint of the currently displayed three-dimensional image is to be changed (rotation or zoom).

The fusional area information storage unit 108 stores fusional area information 108a for obtaining a fusional area according to the depth of the point of gaze. The fusional area information 108a indicates the depth of the point of gaze, and a near side fusion limit and a far side fusion limit which correspond to the depth, for example, as shown in FIG. 12. In other words, the fusional area information 108a indicates positions of a plurality of points of gaze in the depth direction, and a plurality of fusional areas corresponding to the plurality of points of gaze in the depth direction.

The fusional area herein refers to an area where binocular fusion is allowed at one time, without moving the eyes (i.e., without changing the angle of convergence). The fusional area is known as Panum's fusional area.

The fusional area determination unit 109 refers to the fusional area information 108a to determine a fusional area which corresponds to the position of the point of gaze detected by the gaze point detection unit 106. Specifically, the fusional area determination unit 109, for example, refers to the fusional area information 108a of FIG. 12 to obtain a near side fusion limit and a far side fusion limit which correspond to the depth of the point of gaze. Then, the fusional area determination unit 109 determines, as the fusional area, an area that is included in a range defined by the near side fusion limit and the far side fusion limit in the depth direction.

The segmentation unit 110 segments the three-dimensional image in the depth direction, using the output of the depth calculation unit 104 and the fusional area determined by the fusional area determination unit 109. In the present embodiment, the segmentation unit 110 segments the three-dimensional image into three areas which are the fusional area, an area on the nearer side than the fusional area, and an area on the farther side than the fusional area.

The correction process determination unit 111 determines an image processing method for each of the areas obtained by the segmentation unit 110 segmenting the three-dimensional image. Specifically, the correction process determination unit 111, for example, determines an image processing method to suppress display of an object as the image processing method for the areas on the nearer and farther sides than the fusional area.

The image processing unit 112 performs image processing for each area, in accordance with the image processing method determined by the correction process determination unit 111.

As such, the correction process determination unit 111 and the image processing unit 112 perform the processing of correcting the three-dimensional image so as to suppress the display of the object that is included in the three-dimensional image outside the fusional area. In other words, the correction process determination unit 111 and the image processing unit 112 correspond to the correction unit.

The display unit 113 displays the three-dimensional image processed by the image processing unit 112. Examples of the display unit 113 include a three-dimensional display without dedicated glasses (the naked eye) or with dedicated glasses, and a head mounted display. The display unit 113 presents a left-eye image to the left eye and presents a right-eye image to the right eye, thereby achieving three-dimensional display.

<Operation>

Next, the processing operation of the three-dimensional display device 100 configured as set forth above will be described.

Figure 13:
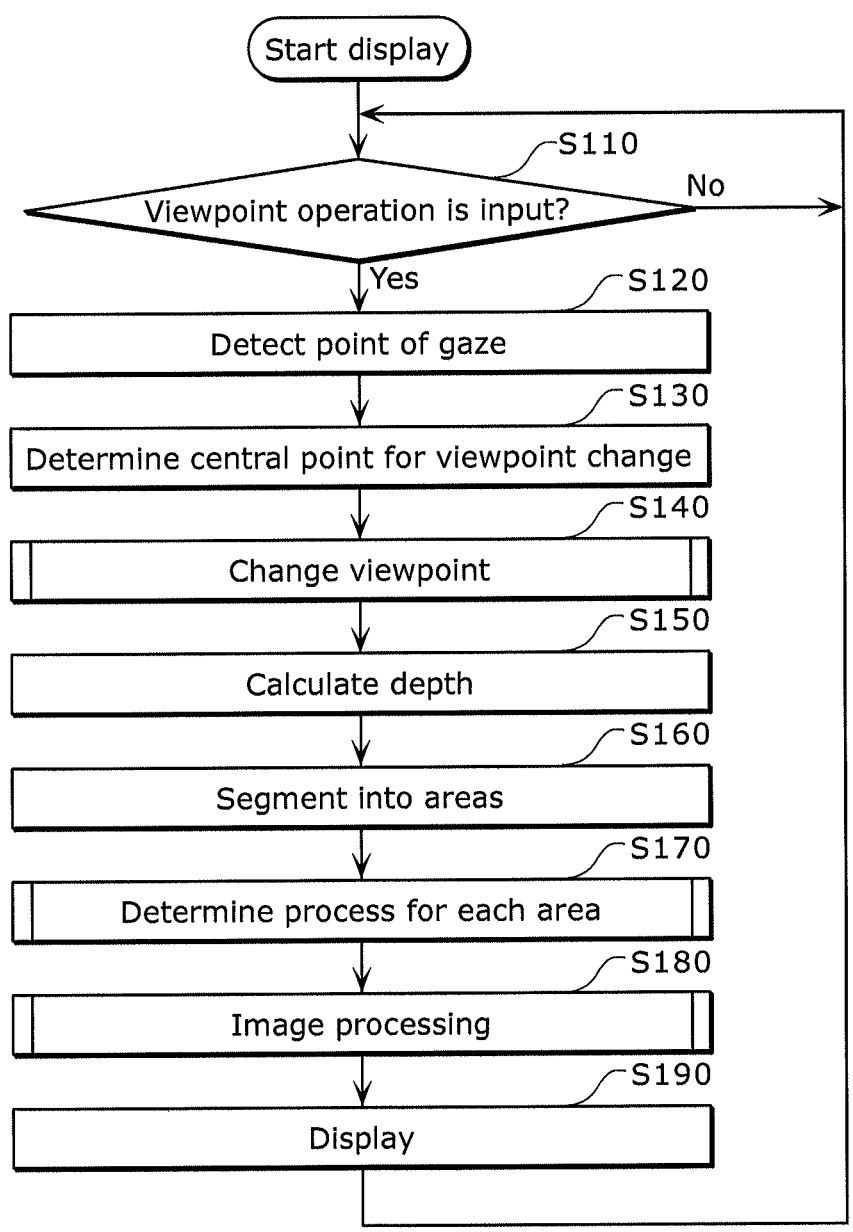
FIG. 13 is a flowchart illustrating processing operation of the three-dimensional display device according to the Embodiment 2

FIG. 13 is a flowchart illustrating processing operation of the three-dimensional display device 100 according to the embodiment 2. The three-dimensional display device 100, for example, starts the following processing, in accordance with a display start indication which is received by display start input means (not shown) from the viewer.

The viewpoint input unit 102 receives input of viewer's viewpoint operation (S110). Step S110 is repeated until input of viewer's viewpoint operation is received. If input of viewpoint operation is received in step S110, the gaze point detection unit 106 detects three-dimensional image coordinates of the point of gaze of the viewer in the three-dimensional image, based on the viewer's eye movement obtained by the sensor 105 (S120). A method to detect the point of gaze will be described below.

The image transformation center determination unit 107 determines the three-dimensional image coordinates of the point of gaze detected in step S120 as three-dimensional image coordinates of the central point for viewpoint change (S130). The central point for viewpoint change is a point a display position at which is unchanged in changing a viewpoint of the three-dimensional image. The three-dimensional image coordinates are transformed into normal coordinates for defining a three-dimensional model in the image information 101a.

The viewpoint changing unit 103 extracts the image information 101*a* on the currently displayed three-dimensional image from the image information storage unit 101. Then, the viewpoint changing unit 103 changes the viewpoint of the displayed three-dimensional image, using the central point for viewpoint change determined in step S130 and a viewpoint specified by the input of the viewpoint operation received in step S110 (S140).

The depth calculation unit 104 calculates the depth of an object, which is included in the three-dimensional image undergone the viewpoint change performed in step S140, in the three-dimensional coordinate system shown in FIG. 11 (S150).

The fusional area determination unit 109 refers to the fusional area information 108*a* to determine a fusional area corresponding to the position of the point of gaze in the depth direction detected in step S120. Then, in accordance with the depth calculated in step S150, the segmentation unit 110 segments the object included in the three-dimensional image into three areas which are an area on the side farther away from the viewer than the fusional area is, the fusional area, and an area on the side closer to the viewer than the fusional area is (S160).

The correction process determination unit 111 allocates correction processes to the respective three areas obtained by segmenting the object in step S160 (S170).

The image processing unit 112 performs, for each area determined in step S170, the correction process on the three-dimensional image undergone the viewpoint change performed in step S140 (S180). Then, the image processing unit 112 outputs the corrected three-dimensional image to the display unit 113.

The display unit 113 displays the three-dimensional image output from the image processing unit 112 (S190).

As such, the viewpoint changing unit 103 changes the viewpoint of the three-dimensional image about the point of gaze of the viewer as the central point, thereby changing the view point of the three-dimensional image so that the object which the viewer is gazing does not move. Thus, the viewpoint changing unit 103 can prevent the viewer from losing, due to the viewpoint change, the object which the viewer is gazing, reducing load imposed on the viewer.

In a conventional method for changing a viewpoint of a three-dimensional image, image information is fixed on a three-dimensional coordinate axis, and the three-dimensional image is rotated or zoomed about a fixed central point (e.g., origin of a fixed coordinate system). This is effective in displaying the three-dimensional image, mapping it into two dimensions, because coordinates in the display screen and coordinates in a space where the viewer exists are independent of each other, the viewer views the display screen as if the viewer looks into a box, and changing a viewpoint is identical to rotating the box and moving the box toward and away from the viewer. On the other hand, in three-dimensional display of a stereo image, a three-dimensional axis of the stereo image is the same as a coordinate axis in the space where the viewer exists. Thus, changing the viewpoint of the three-dimensional image brings a state as if a view around the viewer is transformed. Inherent desire of a viewer in changing a viewpoint is moving a viewer's position relative to an object and changing positions of the viewer's eyes to view the object from a different angle. When the viewer walks around and looks into an object, the gaze object in a field of view of the viewer does not move at the center of the field of view while a coordinate axis which forms the field of view of the viewer rotates or extends and contracts. In three-dimensional image display by stereoscopy, it is necessary to transform the coordinate axis about the point of gaze as if the viewer walks around and looks into the point of gaze, without changing the positions of the viewer's eyes. Thus, as in the present embodiment, the viewpoint of the three-dimensional image is changed about the point of gaze of the viewer as the central point, thereby appropriately changing the viewpoint of the three-dimensional image.

<Detect Point of Gaze>

Hereinafter, a method to detect the point of gaze of the viewer in step S120 will be described in detail.

Information on eye movement depends on a type of the sensor 105. The method to detect the point of gaze depends on information on eye movement. Here, as examples of detection of a point of gaze, methods to detect a point of gaze will be described in respective cases where: (a) the sensor 105 is a stationary camera installed in a housing of a display which includes a screen; (b) the sensor 105 is a proximity camera which is worn by the viewer over the head; (c) the sensor 105 is electrooculogram measuring means which measures eye movement from corneo-retinal potential differences of the eyes by electrodes in contact with a skin; and (d) the sensor 105 is a contact lens with a coil attached thereto.

If the sensor 105 is a stationary camera attached to a display as illustrated in FIG. 8A, the camera captures an image in front of the display at the center. The gaze point detection unit 106 performs face detection on the captured image, thereby extracting a face image of a viewer viewing the display. The gaze point detection unit 106 further extracts images of the viewer's eyes from the extracted face image. Then, the gaze point detection unit 106 identifies positions of pupils or irises in the images of the viewer's eyes and calculates a pupillary distance. The gaze point detection unit 106 obtains a position of a point of gaze on a plane horizontal to the screen from the orientation of the face and the orientations of the midpoints of the eyes at the face detection, and obtains a position of the point of gaze in the depth direction from the pupillary distance.

If the sensor 105 is a camera attached to each of glasses or goggles as illustrated in FIG. 8B, the left and right cameras capture images of the left and right eyes, respectively. The gaze point detection unit 106 obtains orientations of the left and right eyes from the captured left and right images, respectively. The gaze point detection unit 106 obtains, as the point of gaze, a point of intersection of linear lines indicating the respective orientations of the eyes. Alternatively, the gaze point detection unit 106 may derive positions of the pupils of the left and right eyes, derive a position of the point of gaze in the plane horizontal to the screen from components of upward, downward, leftward, and rightward offsets of the pupil positions which are common to the eyes, and obtain a position of the point of gaze in the depth direction from an interocular distance.

If the sensor 105 is an electrooculogram measuring means as illustrated in FIG. 9, electrodes for measuring electrooculograms are attached in contact with both sides of each eye and a forehead above and a cheek below at least one eye. Then, the electrooculogram measuring means measures changes in potential associated with eye movements in the horizontal direction from two electrodes attached on the both sides of each eye. Then, the electrooculogram measuring means measures changes in potential associated with eye movement in the vertical direction from the two electrodes attached on skins above and below the eye. The gaze point detection unit 106 derives a position of the point of gaze in the plane horizontal to the screen from components of changes in potential which are common to the eyes, and derives a position of the point of gaze in the depth direction from components of changes in potential which are in antagonism in the horizontal direction between the eyes.

If the sensor 105 is a contact lens with a coil attached thereto as illustrated in FIG. 10, the sensor 105 measures, for each eye, changes in distribution of potential associated with eye movement from the coil. The gaze point detection unit 106 derives a position of the point of gaze in the plane horizontal to the screen from components of changes in potential which are common to both eyes, and derives a position of the point of gaze in the depth direction from components of changes in potential which are in antagonism in the horizontal direction between the eyes.

It should be noted that the method to detect a point of gaze is not limited to the above methods. For example, the gaze point detection unit 106 may detect a point of gaze, using, as the sensor 105, myopotential measuring means which measures movements of muscles around the eyes from electrodes in contact with a skin. Moreover, the gaze point detection unit 106 may detect a point of gaze, based on potential associated with pupil motility induced by a contact lens embedded with a magnetic coil. Moreover, the gaze point detection unit 106 may detect a point of gaze from potential associated with accommodation of crystalline lens induced by a magnetic coil. Moreover, the gaze point detection unit 106 may detect a point of gaze, using some combinations of the plurality of detection methods described above.

<Viewpoint Change>

Figure 14:
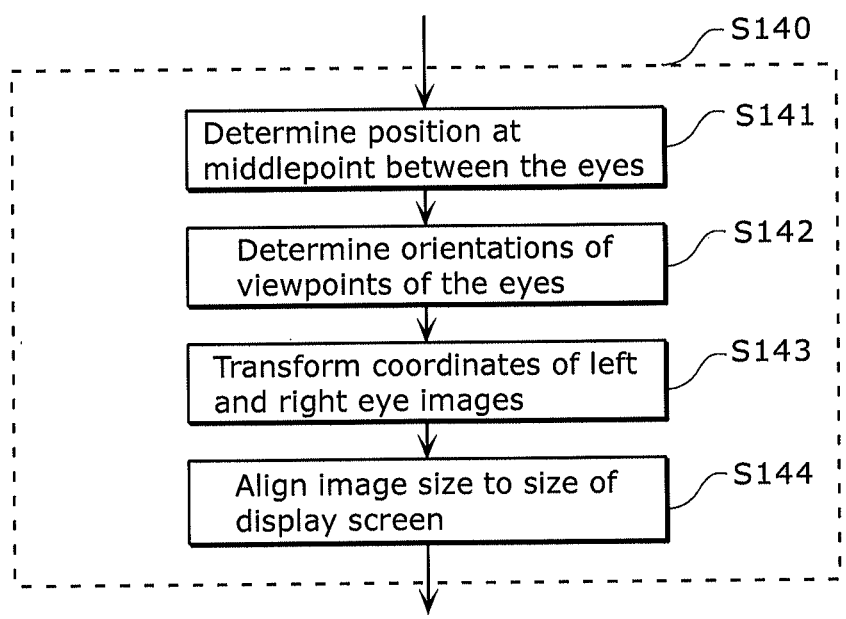
FIG. 14 is a flowchart illustrating processing operation of a viewpoint changing unit according to the embodiment 2.

FIG. 14 is a flowchart illustrating processing operation of the viewpoint changing unit 103 according to the embodiment 2. In other words, FIG. 14 illustrates details of step S140. Hereinafter, an example of a method to change the viewpoint of the three-dimensional image in step S140 will be described in detail.

The three-dimensional image is, as shown in FIG. 7, generated using the image information 101a in which coordinates indicating a position of a point in a standard coordinate system representing a three-dimensional space and a display color of the point are paired. The image information 101a includes at least information on coordinates indicating positions of points on a surface of the object.

Figure 15:
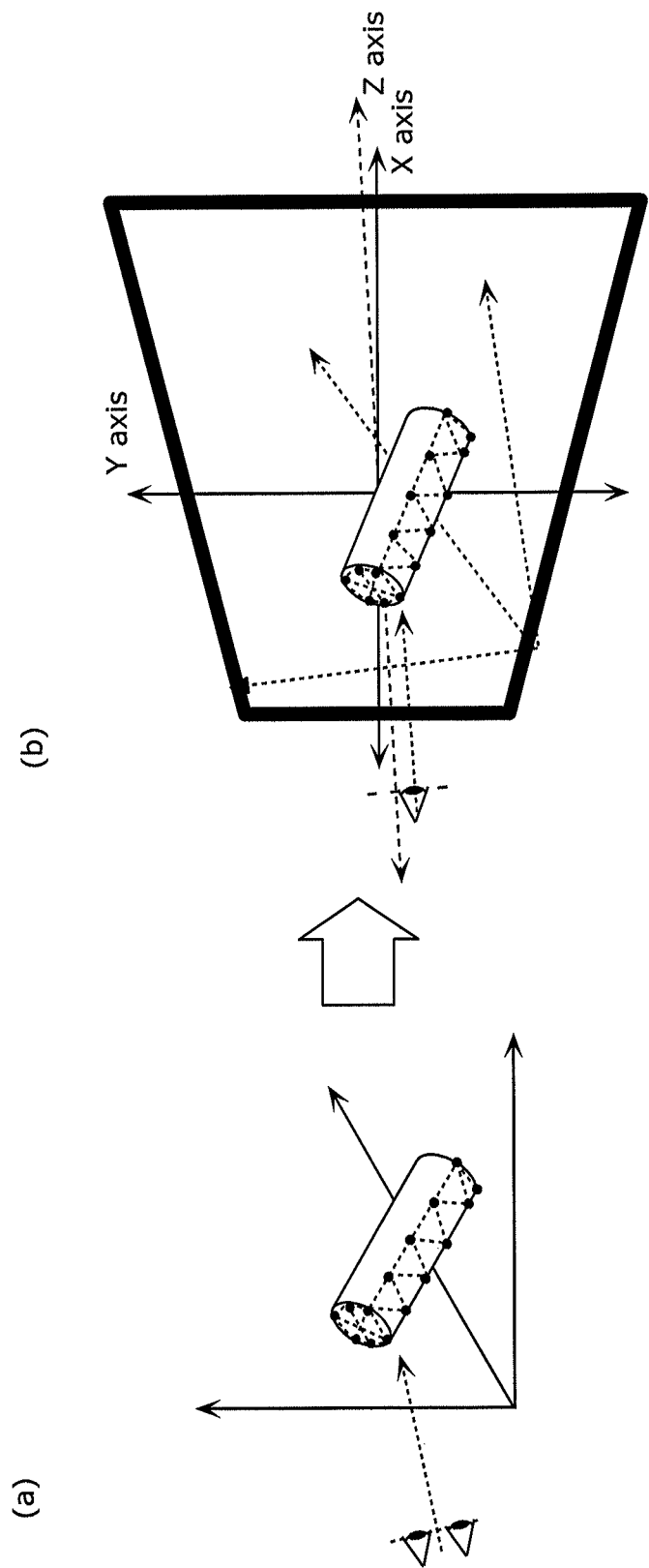
FIG. 15 shows schematic views illustrating an example of coordinate transformation according to the embodiment 2.

For example, polygon rendering is used in the image generation process. In polygon rendering, three-dimensional shape data is represented by a group of polygons. The three-dimensional image is generated by performing a rendering process using the image information 101a as shown in FIG. 7 represented by vertex coordinates of polygons. In polygon rendering, an object is represented by triangular planes each formed of three points. For example, as shown in (a) of FIG. 15, an object is represented by placing triangles in the standard coordinate system. A processing unit includes the plane and vertex coordinates of each triangle. Polygon rendering is a general one as a three-dimensional graphics method.

The viewpoint changing unit 103, first, determines a position at the middlepoint of a line segment extending between the viewer's left and right eyes in the standard coordinate system, based on the viewpoint operation input in step S110 and the central point for viewpoint change determined in step S130 (S141). The viewpoint changing unit 103 sets the middlepoint between the eyes to the viewpoint, as shown in (a) of FIG. 15. Next, the viewpoint changing unit 103 determines positions of both eyes. The viewpoint changing unit 103 sets a distance between the viewer's left and right eyes to 6.5 cm, for example. The viewpoint changing unit 103 determines the positions of both eyes on a linear line parallel with the horizontal axis (i.e., the X axis of FIG. 11) of the display image so that the position determined in step S141 is in the middle of the eyes. The viewpoint changing unit 103 rotates the axes of the normal coordinates to align with the orientations of the axes of the three-dimensional display coordinates as shown in (b) of FIG. 15.

The viewpoint changing unit 103 determines orientations from the positions of both eyes to the central point for viewpoint change determined in step S130, and viewing angles of both eyes, and determines a display size of the object (S142). If the viewpoint operation input in step S110 includes zoom operation, the viewpoint changing unit 103 resizes the display size of the object at which time the viewpoint changing unit 103 does not change the positions of the eyes of the viewer viewing the image.

Furthermore, the viewpoint changing unit 103 transforms the coordinates so that a line extending between the position at the middlepoint between the viewer's left and right eyes determined in step S141 and the central point for viewpoint change determined in step S130 is parallel with the Z axis of FIG. 11 (S143). The viewpoint changing unit 103 performs the coordinate transformation, assuming that the viewer views the image in front of the screen.

In the coordinates obtained by the transformation in step S143, the viewpoint changing unit 103 determines a range (size) of the object that can be projected onto the screen in accordance with the positions and orientations of the eyes (S144).

<Determine Correction Process>

Figure 16:
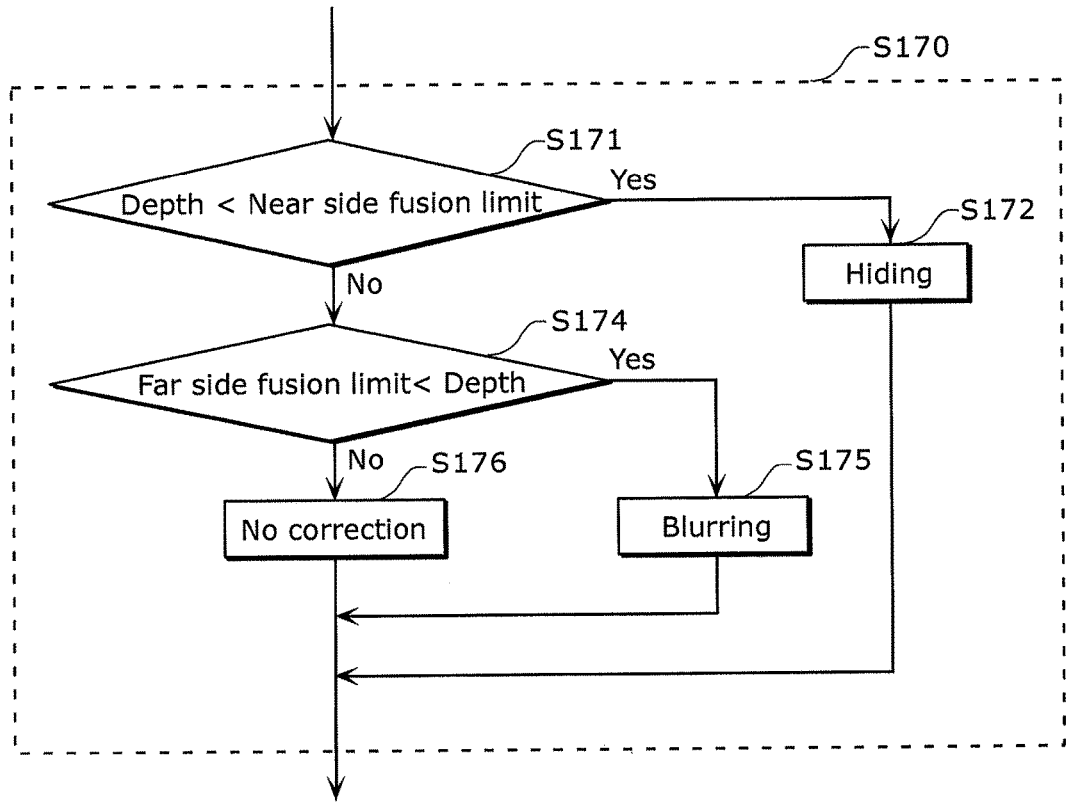
FIG. 16 is a flowchart illustrating processing operation of a correction process determination unit according to the embodiment 2.

FIG. 16 is a flowchart illustrating processing operation of the correction process determination unit 111 according to the embodiment 2. In other words, FIG. 16 illustrates details of step S170.

The correction process determination unit 111 determines a correction process to be performed on each of three areas obtained as a result of the segmentation in step S160. In other words, the correction process determination unit 111 determines a correction process to be performed on each point on the surface of the object included in the three-dimensional image undergone the viewpoint change performed in step S140. It should be noted that in the present embodiment, the segmentation is performed by comparing a Z-coordinate value in the coordinate system of FIG. 11 with the fusional area.

First, the correction process determination unit 111 determines whether the point on the surface of the object included in the three-dimensional image is included in an area which has a depth value smaller than the near side fusion limit (S171). In other words, the correction process determination unit 111 determines whether a Z-coordinate value of the point in the coordinate system of FIG. 11 which indicates a position on a side closer to the viewer's eyes than a position, indicated by a Z-coordinate value of the near side fusion limit, is.

If the Z-coordinate value of the point indicates a position on the side closer to the viewer's eyes than the position indicated by the Z-coordinate value of the near side fusion limit is (Yes in S171), the correction process determination unit 111 determines that a correction process to be performed on that point is hiding the point (S172). The hiding refers to removing the point from the display range. In this case, a surface of the object where that point is included is handled as if transparentized.

On the other hand, if the Z-coordinate value of the point is equal to the Z-coordinate value of the near side fusion limit or indicates a position on the side farther away from the viewer's eyes (No in S171), the correction process determination unit 111 determines whether the Z-coordinate value of the point indicates a position on the side farther away from the viewer's eyes than a position, indicated by the Z-coordinate value of the far side fusion limit, is (S174).

If the Z-coordinate value of the point indicates a position on the side farther away from the viewer's eyes than the position, indicated by the Z-coordinate value of the far side fusion limit, is (Yes in S174), the correction process determination unit 111 determines that a correction process to be performed on that point is blurring (S175). On the other hand, if the Z-coordinate value of the point is equal to the Z-coordinate value of the far side fusion limit or indicates a position on the side closer to the viewer's eyes than the position, indicated by the Z-coordinate value of the far side fusion limit, is (No in S174), the correction process determination unit 111 determines that the correction process is not to be performed on that point (S176).

It should be noted that specifically, for example, the blurring is a process of low pass filtering a target area to reduce a spatial frequency. The lower the low pass frequency is the greater an extent to which the target area is blurred. Another example of the blurring is a process of mixing and blurring different images A and B, which are respectively a right-eye image and a left-eye image, and display resultant images. As blurring, for example, a process can be used in which a value of color information at each coordinate point of the target area is blurred using an intermediate color of color information of the image A and color information of the image B. A degree of the blurring is determined based on a ratio of mixing the color of one of the images to the other. The degree of the blurring is largest when the mixing ratio is 1:1.

<Image Processing>

Figure 17:
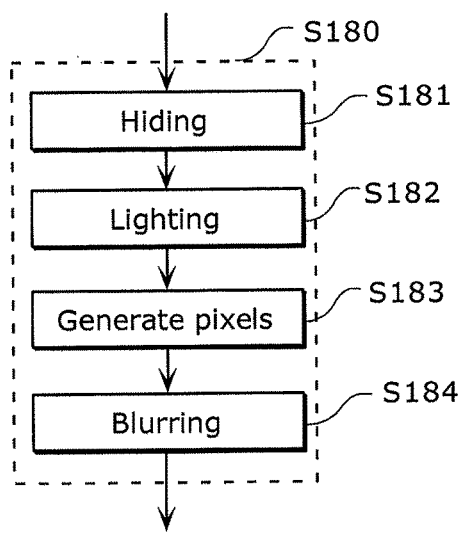
FIG. 17 is a flowchart illustrating processing operation of an image processing unit according to the embodiment 2.

FIG. 17 is a flowchart illustrating processing operation of the image processing unit 112 according to the embodiment 2. In other words, FIG. 17 illustrates details of step S180.

The image processing unit 112 hides an object located in an area on a nearer side than a plane which is in parallel with the display screen and includes the near side fusion limit (S181). In polygon rendering, points within that area are removed from a range for image generation, thereby hiding the object. Moreover, the image processing unit 112 can generate an image of the blood vessel's cross-section and inside the blood vessel if the image information 101a includes data of points inside the blood vessel.

Next, the image processing unit 112 performs polygon rendering on the three-dimensional image (the three-dimensional model) undergone the viewpoint change performed in step S140, thereby generating a right-eye image and a left-eye image. In other words, the image processing unit 112 applies lighting to the three-dimensional model, in which the object included in the area on the nearer side than the fusional area is hidden, by a light source which has an attribute and a fixed position on a display coordinate axis (S182).

Using light of a solid-state light source and a display color for each of coordinate points included in the image information 101a, the image processing unit 112 determines a color of each coordinate point. Subsequently, the image processing unit 112 generates triangles which form a polygon, and fill the triangles with pixels. The filling interpolates a color for each pixel based on colors of vertices (S183). The image processing unit 112 applies blurring, by low pass filtering, to each of the pixels generated by the points included in the area on the farther side than the fusional area (i.e., the area on the side farther away from the viewer) (S184).

An object located on the farther side than the fusional area also causes double vision. However, an object located on a farther side than the point of gaze does not hide the object located at the point of gaze. Thus, while double vision does not significantly impede the viewer from seeing the object located at the point of gaze, the viewer feels uncomfortable, experiencing double vision.

An increase in depth does not necessarily increase a disparity of an object to infinity. The human eyes converge to see an object. However, in an opposite movement, which is looking into the distance (divergence), the left and right eyes does not move to angles at which the left and right eyes are in opposite directions. A state where the divergence is at a maximum value indicates that viewing directions of the left and right eyes are parallel with each other. Thus, changes in disparity corresponding to changes in depth on a far side in the three-dimensional image are small as compared to changes in disparity corresponding to changes in depth on a near side. Thus, double vision on the far side is not as large as double vision produced on the near side.

Thus, the image processing unit 112, in step S184, blurs an object located on the farther side than the fusional area by, for example, a method of lowering a spatial frequency by a filtering process to cause the object fell into a state acceptable as a background image.

The image processing unit 112 performs processing on the right-eye image and the left-eye image in step S180 to generate a stereoscopic image.

FIG. 18 shows diagrams illustrating examples of the three-dimensional image which is displayed by the three-dimensional display device 100 according to the embodiment 2. Specifically, (a) of FIG. 18 shows an uncorrected three-dimensional image, and (b) of FIG. 18 shows a corrected three-dimensional image.

As FIG. 18 shows, when a blood vessel is displayed as if extending from the front of the screen into the back as illustrated in (b) of FIG. 1, the three-dimensional display device 100 can prevent a near side portion of the blood vessel from looking double as illustrated in (a) of FIG. 18. Furthermore, the three-dimensional display device 100 can display an image of a cross-section of the blood vessel cut along a plane of the near side fusion limit as illustrated in (b) of FIG. 18. This allows the three-dimensional display device 100 to display a junction between the removed near side portion of the blood vessel and a portion within the fusional area so that the junction appears natural.

<Effects>

As described above, according to the three-dimensional display device 100 of the present embodiment, the viewpoint changing unit 103 changes the view point of the three-dimensional image using the point of gaze of the viewer as the central point for the viewpoint change, thereby achieving viewpoint movement about the point of gaze. Furthermore, the three-dimensional display device 100 can determine a fusional area in accordance with a position of the point of gaze, remove an object located on the nearer side than the fusional area, and blur an object located on the farther side than the fusional area. This can suppress the occurrence of double vision produced by the objects located outside the fusional area. Furthermore, the three-dimensional display device 100 can improve the visibility of an object located at the point of gaze by removing an object on the nearer side that is hiding the object located at the point of gaze. By blurring an object located on the farther side than the fusional area, the three-dimensional display device 100 can also correct the three-dimensional image so that the presence of the blurred object is known as a blur background image. This allows the three-dimensional display device 100 to avoid an image after the viewpoint change from causing discomfort to the viewer as if the image has the same depth perception as that produced by an image before the viewpoint change. From the above, the three-dimensional display device 100 can change the viewpoint of the three-dimensional image so that the object located at the point of gaze does not move, ensuring the visibility of the object located at the point of gaze and retaining the naturalness throughout the image.

In the present embodiment, the fusional area information 108a is pre-stored in the fusional area information storage unit 108. An area where the fusion occurs without moving the eyes may vary from individual to individual. Moreover, it is necessary that a viewer can reliably ascertain the context of the blood vessel described in the present embodiment when viewing the image of the blood vessel. Thus, a narrower fusional area is more suitable. Moreover, a fusional area of the same individual may vary over time due to fatigue and so on. Thus, the fusional area determination unit 109 may store time-series data of the fusional area when the viewer is viewing a three-dimensional video into the fusional area information storage unit 108, and determine a fusional area narrower than the stored fusional areas. In particular, correction of a three-dimensional video using a narrower fusional area is effective for use in a long surgery or the like in operation.

While in the present embodiment, the three-dimensional image includes a blood vessel object representing a blood vessel, it should be noted that the three-dimensional image may not include a blood vessel object. For example, the three-dimensional image may include objects of tissues of the abdomen, the thorax, or the head, for example. By including objects of body regions different from blood vessels in the three-dimensional image as such, the three-dimensional display device 100 is applicable to surgeon simulators for surgical preparation or educational purpose.

A surgeon simulator, as with PTL 3 (International Publication WO2010/021309), for example, stores three-dimensional image data of patient's body in association with elasticity data and so on, and deforms and displays a polygon model image in accordance with surgical procedure such as incision. In the surgeon simulator also, when, for example, a viewer is viewing a simulation image of a patient's abdomen, as the viewer changes the viewpoint from a side of the patient toward the head, the thorax and the head are located on nearer sides to the viewer than abdominal organs gazed by the viewer. In such a case, body parts located on the near sides look double, not only hiding an organ at the point of gaze but also making the viewer feel discomfort by flicker or the like.

Thus, application of the three-dimensional display device 100 according to the present embodiment to the surgeon simulator suppresses display of objects located outside a fusional area, thereby displaying a three-dimensional image without causing discomfort to the viewer, while retaining information on arrangement of organs.

While in the present embodiment, the operation of the three-dimensional display device 100 has been described in terms of rotation of an image of a blood vessel by way of example of the viewpoint change, it should be noted that the viewpoint change may be a process other than rotation, such as a zoom operation. Operation of the three-dimensional display device 100 in a zoom process on an image of a blood vessel is the same as that at rotation of an image. If the zoom process is input in step S110, a point of gaze of a viewer is detected in step S120 and set to a central point for the zoom process in step S130. The zoom process is performed in step S140 by the viewer moving a position at the middlepoint between the eyes closer to or away from the point of gaze, and thereby the viewpoint of the three-dimensional image is changed.

Figure 19:
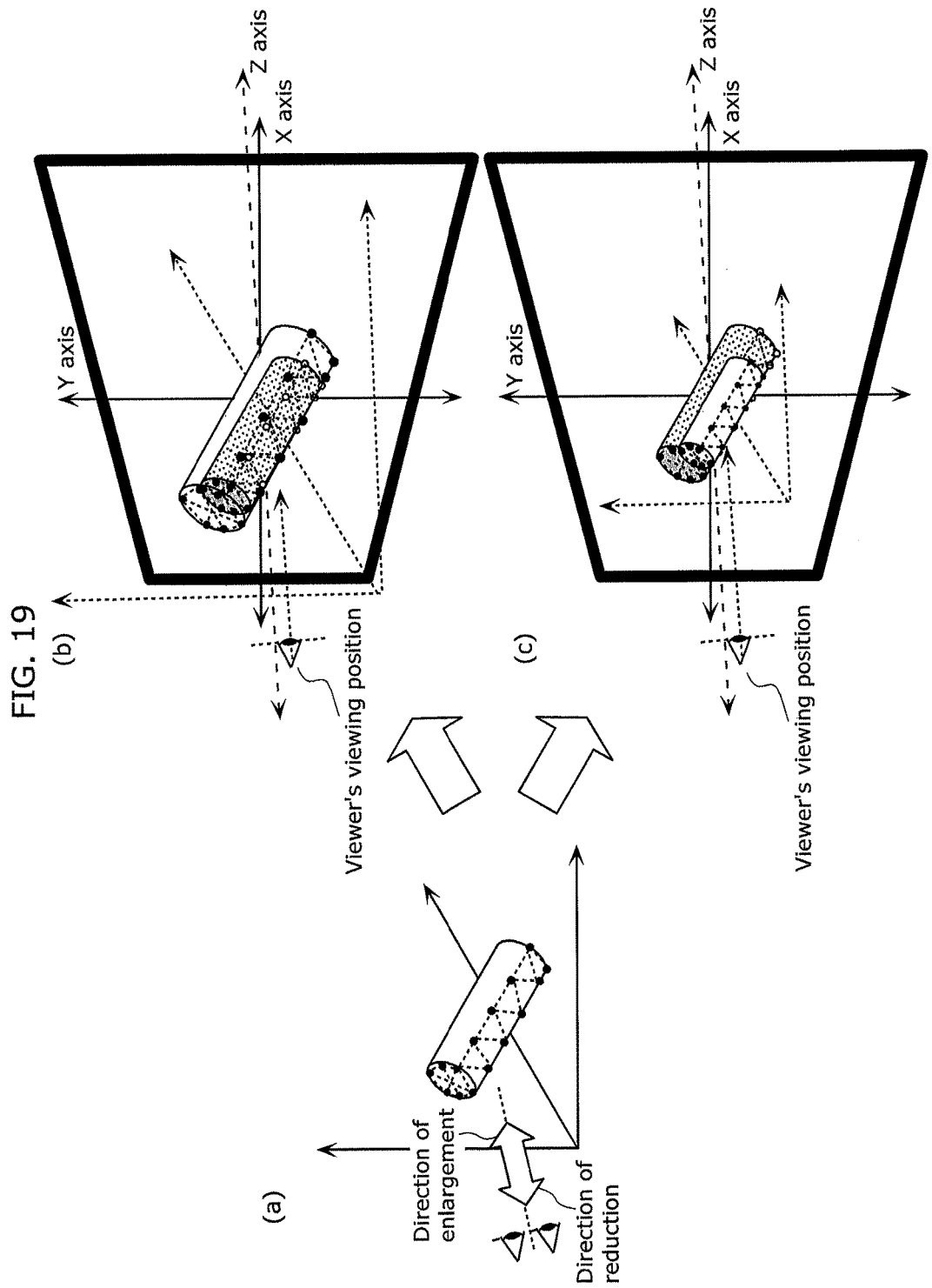
FIG. 19 shows schematic views for illustrating viewpoint change according to a variation of the embodiment 2

FIG. 19 shows schematic views for illustrating viewpoint change according to a variation of the embodiment 2. Specifically, FIG. 19 is a schematic view of the zoom process. Part (a) of FIG. 19 illustrates a relationship between the zoom process (enlarging or reducing) and a direction of movement of the viewpoint in the standard coordinate system. In the standard coordinate system, the closer the coordinate position of the viewpoint is to a coordinate position of an object, the greater the image of the displayed object is enlarged. The farther the coordinate position of the viewpoint is away from the coordinate position of the object in the standard coordinate system, the smaller the size of the image of the displayed image is reduced.

Part (b) of FIG. 19 is a schematic view of changes in display in the three-dimensional display coordinate system at the enlargement process. The dotted cylinder is an object before the viewpoint change, and the white cylinder is an object after the enlargement process. The enlargement process moves the near side of the cylinder closer to a viewer's viewing position and moves the far side of the cylinder farther away from the viewing position.

Part (c) of FIG. 19 is a schematic view of changes in display in the three-dimensional display coordinate system at the reduction process. Similarly to (b) of FIG. 19, the dotted cylinder is an object prior to the viewpoint change, and the white cylinder is an object after the reduction process. The reduction process moves the near side of the cylinder farther away from a viewer's viewing position and moves the far side of the cylinder closer to the viewing position.

As the example of FIG. 19 shows, the zoom process also changes a depth range of an object. Thus, effects similar to that obtained from the rotation process can be achieved by performing, similarly to the rotation process, image processing on a three-dimensional image based on a fusional area.

Embodiment 3

In the present embodiment, a three-dimensional image includes a plurality of blood vessel objects representing a plurality of blood vessels. A three-dimensional display device corrects the three-dimensional image, based on the importance levels of blood vessel objects.

Figure 20:
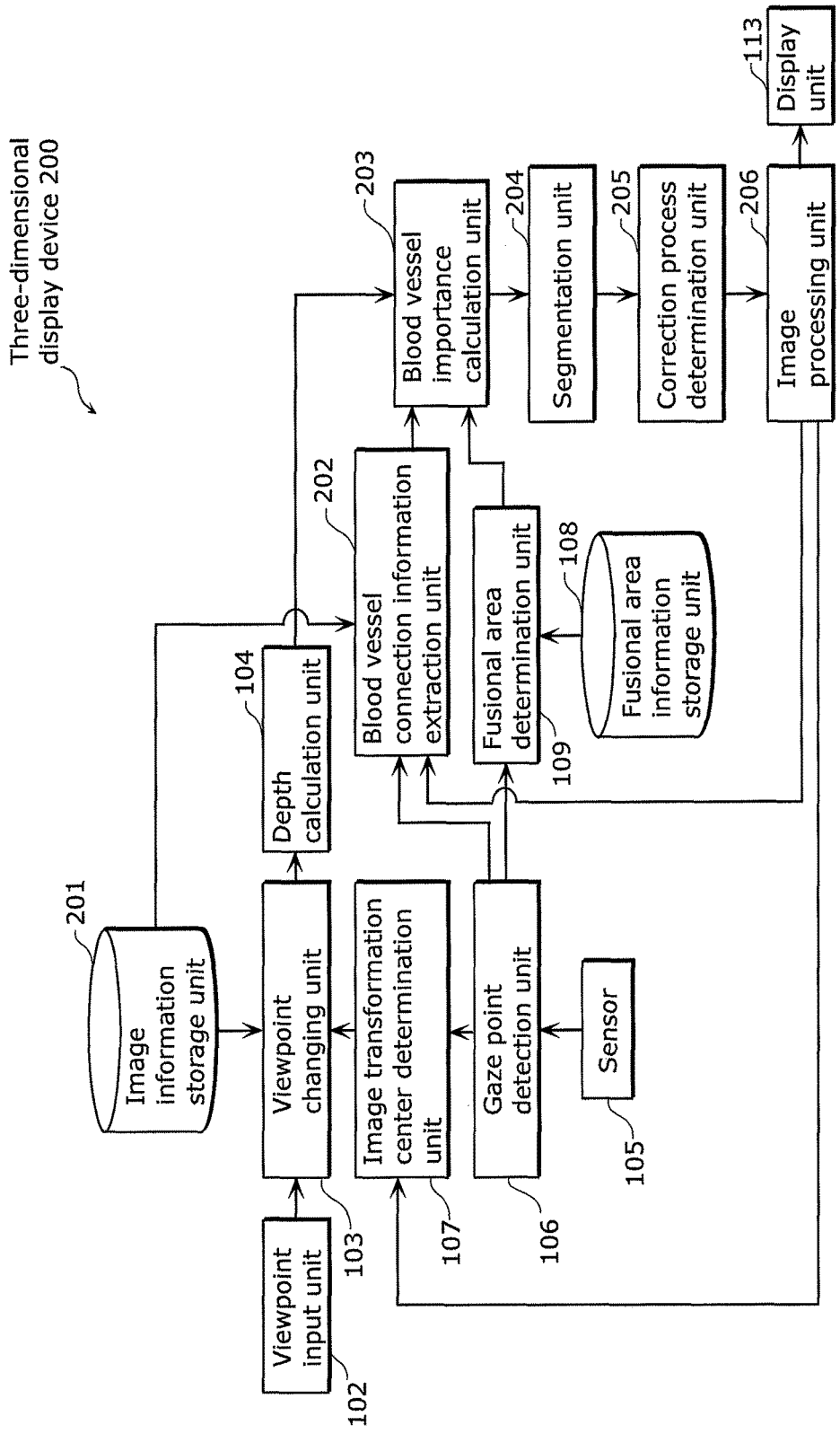
FIG. 20 is a block diagram of a functional configuration of a three-dimensional display device according to an embodiment 3.

FIG. 20 is a block diagram of a functional configuration of a three-dimensional display device 200 according to an embodiment 3.

The three-dimensional display device 200 includes an image information storage unit 201, a viewpoint input unit 102, a viewpoint changing unit 103, a depth calculation unit 104, a sensor 105, a gaze point detection unit 106, an image transformation center determination unit 107, a fusional area information storage unit 108, a fusional area determination unit 109, a blood vessel connection information extraction unit 202, a blood vessel importance calculation unit 203, a segmentation unit 204, a correction process determination unit 205, an image processing unit 206, and a display unit 113.

The image information storage unit 201 is, for example, a hard disk drive or a semiconductor memory. The image information storage unit 201 stores image information 201a on a three-dimensional image which is displayed.

Figures 21, 22:
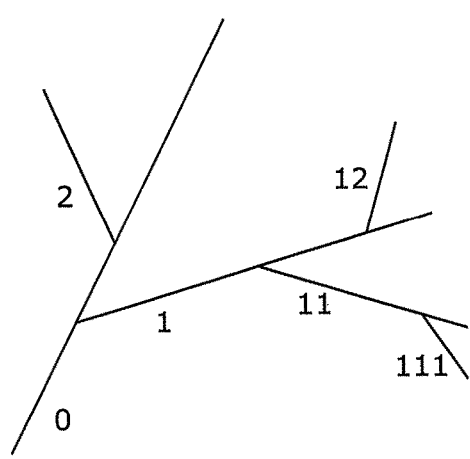
FIG. 21 is a diagram showing an example of image information in the embodiment 3.
FIG. 22 is a schematic view illustrating an example of a method to determine a branch number according to the embodiment 3.

The image information 201a includes information representing three-dimensional models of the blood vessel objects and connection information indicating connectivity between the blood vessel objects. Specifically, the image information 201a includes coordinates of points on each blood vessel object, a display color, a blood vessel ID, and a branch number, for example, as shown in FIG. 21.

The blood vessel connection information extraction unit 202 is by way of example of a blood vessel connection information obtaining unit. The blood vessel connection information extraction unit 202 refers to the image information 201a to obtain connection information indicative of connectivity of a blood vessel object located at a point of gaze to each of the blood vessel objects included in the three-dimensional image. Specifically, the blood vessel connection information extraction unit 202 extracts, from the image information 201a, connection information of the blood vessel object which the viewer is gazing with other blood vessel objects, based on coordinate information of the point of gaze of the viewer detected by the gaze point detection unit 106 and positions of the blood vessel objects on a currently displayed three-dimensional image.

The blood vessel importance calculation unit 203 calculates the importance of each of the blood vessel objects in the three-dimensional image, based on a fusional area determined by the fusional area determination unit 109, the connection information extracted by the blood vessel connection information extraction unit 202, and depth information of the blood vessel object.

Specifically, the blood vessel importance calculation unit 203 calculates, for each of the blood vessel objects, the importance of the blood vessel object so that the blood vessel object, if included in the fusional area, is of higher importance than if the blood vessel object is not included in the fusional area.

Moreover, the blood vessel importance calculation unit 203 may calculate, for each of the blood vessel objects, the importance of the blood vessel object so that, for example, the blood vessel object having a less number of blood vessel branches to the blood vessel object located at the point of gaze is of higher importance, wherein the number of blood vessel branches is the number of branches and connections of a blood vessel which appear when connecting two blood vessel objects in a shortest path.

Moreover, the blood vessel importance calculation unit 203 may calculate, for each of the blood vessel objects, the importance of the blood vessel object so that, for example, the blood vessel object having a smaller spatial distance to the blood vessel object located at the point of gaze is of higher importance.

The segmentation unit 204 segments the three-dimensional image into areas in a depth direction, in accordance with the importance levels of the blood vessel objects calculated by the blood vessel importance calculation unit 203.

The correction process determination unit 205 determines how to process the three-dimensional image for each of the areas obtained by the segmentation by the segmentation unit 204.

In other words, the correction process determination unit 205 and the image processing unit 112 perform processing to correct the three-dimensional image so that display of a blood vessel object the importance of which is lower is suppressed to a greater extent.

The image information 201a shown in FIG. 21 includes coordinates of points on each blood vessel object, a display color, a blood vessel ID, and a branch number. The coordinates are expressed in the standard coordinate system. The display color indicates a display color of a corresponding point. The blood vessel ID is a sign or a number uniquely attached to a blood vessel object in the three-dimensional image.

The branch number is set according to a predetermined rule and indicates connectivity between blood vessels. In other words, the branch number corresponds to the connection information. For example, as shown in FIG. 22, the branch number "0" is attached to the origin of the blood vessel in the image and single-digit numbers in sequence are attached to blood vessels sequentially branching off from the blood vessel that have the branch number "0." Furthermore, the number of digits to be attached to a branch number is increased each time the blood vessel branches. The number of digits of the branch number attached as such indicates the number of times the blood vessel branches off starting from the origin. In other words, the branch number indicates connectivity between the blood vessels.

It should be noted that the expression of the branch information is not limited to the above. The expression of branch information (the connection information) may be other than the above expression, insofar as a blood vessel object from which each blood vessel object has branched off can be determined.

Figure 23:
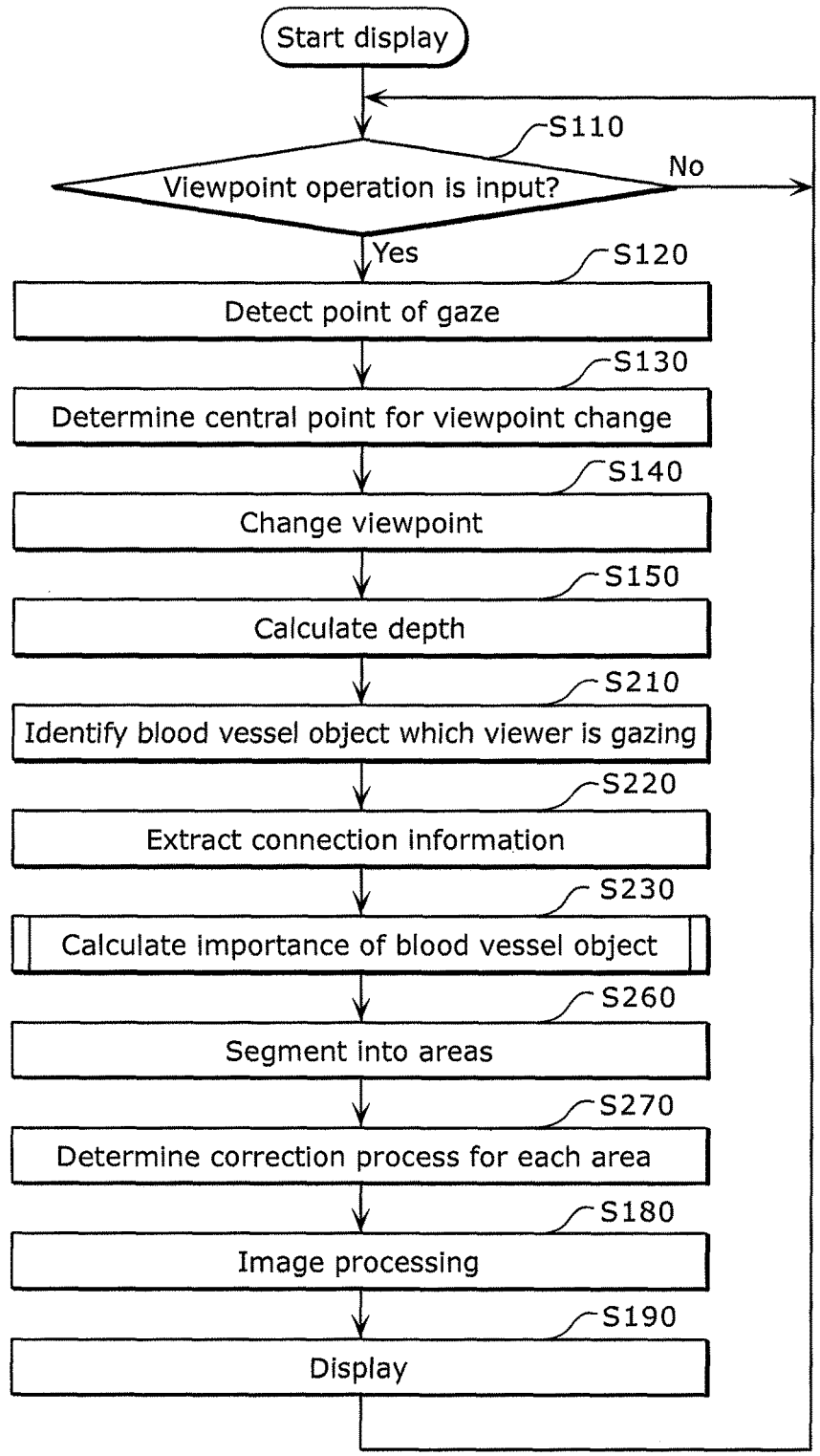
FIG. 23 is a flowchart illustrating processing operation of the three-dimensional display device according to the embodiment 3.

FIG. 23 is a flowchart illustrating processing operation of the three-dimensional display device 200 according to the embodiment 3.

After processing of steps S110 to S150 is performed, the blood vessel connection information extraction unit 202 identifies a blood vessel object which the viewer is gazing, using coordinates indicating a position of the point of gaze of the viewer detected in step S120, the currently displayed three-dimensional image, and normal coordinates in the image information 201a (S210). The blood vessel connection information extraction unit 202 further refers to the image information 201a to extract connection information indicating connectivity between the blood vessel object which the viewer is gazing and each of the plurality of blood vessel objects included in the three-dimensional image (S220).

The blood vessel importance calculation unit 203 calculates the importance of each of the blood vessel objects included in the three-dimensional image, based on the connection information extracted in step S220 and the fusional area (S230). The segmentation unit 204 segments the three-dimensional image into a plurality of areas, based on the importance levels calculated in step S230 (S260). The segmentation unit 204 attaches importance levels to the areas and outputs the importance levels.

The correction process determination unit 205 determines a correction process for each area obtained by the segmentation in step S260 (S270). The correction process is determined according to the importance of the area.

Figure 24:
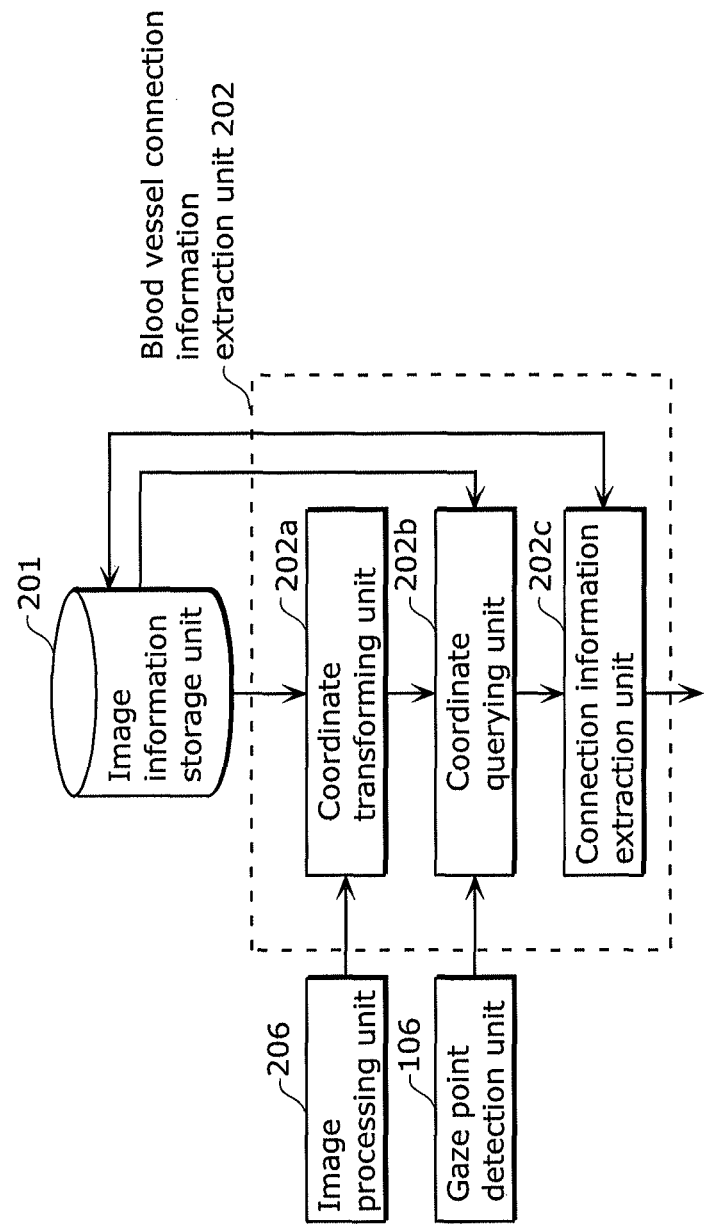
FIG. 24 is a block diagram of a detailed functional configuration of a blood vessel connection information extraction unit according to the embodiment 3.

FIG. 24 is a block diagram of a detailed functional configuration of the blood vessel connection information extraction unit 202 according to the embodiment 3. The blood vessel connection information extraction unit 202 includes a coordinate transforming unit 202a, a coordinate querying unit 202b, and a connection information extraction unit 202c.

In step S220, first, the coordinate transforming unit 202a obtains the currently displayed three-dimensional image and coordinate information of the three-dimensional image from the image processing unit 206. Furthermore, the coordinate transforming unit 202a obtains the image information 201a corresponding to the currently displayed three-dimensional image from the image information storage unit 201. Furthermore, the coordinate transforming unit 202a transforms normal coordinates included in the image information 201a into display coordinates of the currently displayed three-dimensional image. Next, the coordinate querying unit 202b obtains the coordinates of the point of gaze of the viewer from the gaze point detection unit 106. Then, the coordinate querying unit 202b compares the blood vessel object the normal coordinates of which has been transformed into the display coordinates of the currently displayed three-dimensional image and the point of gaze of the viewer. The coordinate querying unit 202b identifies a blood vessel object located at a coordinate position that is closest to the point of gaze, as the blood vessel object which the viewer is gazing. Furthermore, the coordinate querying unit 202b extracts a blood vessel object within a predetermined proximity from the point of gaze as a blood vessel object proximate to the point of gaze. The connection information extraction unit 202c extracts a blood vessel object leading to the blood vessel object identified as the blood vessel object which the viewer is gazing, based on the blood vessel ID and the branch number that are included in the image information 201a. For example, the connection information extraction unit 202c extracts, among data items that have the same blood vessel ID as the blood vessel ID of the blood vessel object which the viewer is gazing, a data item having a branch number the leftmost digit of which is the same as that of the blood vessel object which the viewer is gazing, thereby extracting a blood vessel object which has branched off, from the origin of the blood vessel, at the same location as the blood vessel object which the viewer is gazing.

Figure 25:
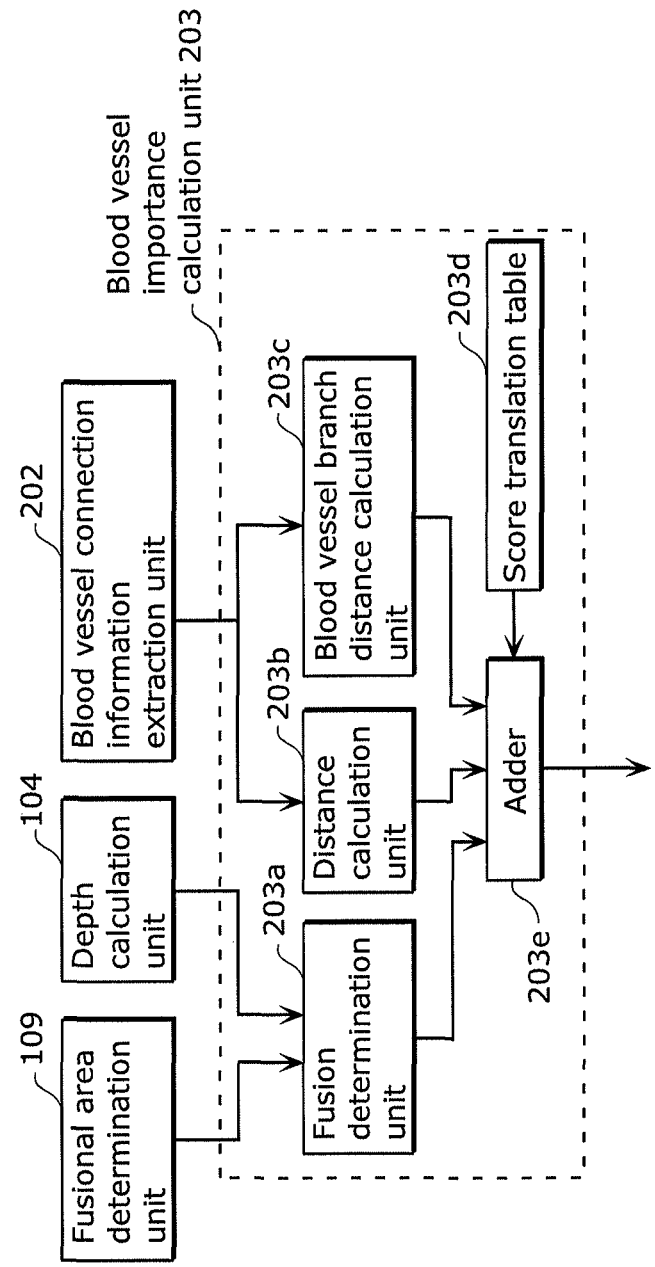
FIG. 25 is a block diagram of a detailed functional configuration of a blood vessel importance calculation unit according to the embodiment 3.

FIG. 25 is a block diagram of a detailed functional configuration of the blood vessel importance calculation unit 203 according to the embodiment 3.

The blood vessel importance calculation unit 203 includes a fusion determination unit 203a, a distance calculation unit 203b, a blood vessel branch distance calculation unit 203c, a score translation table 203d, and an adder 203e.

Figure 26:
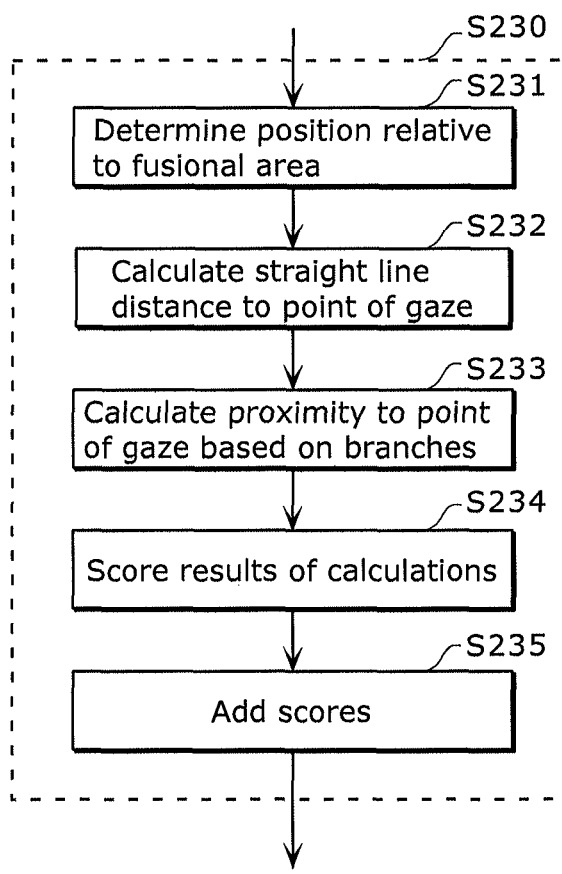
FIG. 26 is a flowchart illustrating processing operation of the blood vessel importance calculation unit according to the embodiment 3.

FIG. 26 is a flowchart illustrating processing operation of the blood vessel importance calculation unit 203 according to the embodiment 3.

First, using the depth (i.e., a Z coordinate value) of each point on the object in the display coordinate system calculated in step S150, a depth position of the near side fusion limit, and a depth position of the far side fusion limit obtained in step S120, the fusion determination unit 203a determines if the point on the blood vessel object is located on the nearer side than the fusional area, within the fusional area, or on the farther side than the fusional area (S231).

The distance calculation unit 203b calculates, for each point on the blood vessel object extracted in step S220, an Euclidean distance between that point and the point of gaze (S232).

The blood vessel branch distance calculation unit 203c calculates a branch distance of each blood vessel object extracted in step S220 to the blood vessel object which the viewer is gazing identified in step S210 (S233). The branch distance indicates the number of branches. The branch distance is calculated from a branch number, for example. Specifically, the blood vessel branch distance calculation unit 203c compares a branch number of each blood vessel object and the branch number of the blood vessel object which the viewer is gazing, and calculates a branch distance therebetween by summing up values which are obtained by multiplying the leftmost digit of the branch number by 10,000, the second leftmost digit by 1,000, the third leftmost digit by 100, and the fourth leftmost digit by 10. If the number of digits of one of branch numbers to be compared therebetween is less than the other, the blood vessel branch distance calculation unit 203c calculates a branch distance, assuming that the lacking digit to be compared is zero.

It should be noted that the method to calculate a branch distance is not limited to the above method as it can quantitatively determine how far to branch back the blood vessels from two points on blood vessel objects to reach a same blood vessel.

The adder 203e refers to the score translation table 203d to obtain scores respectively corresponding to the result of the determination in step S231, the spatial distance calculated in step S232, and the branch distance calculated in step S233 (S234). The score translation table 203d includes scores (incremented or decremented) corresponding to factors which determines the importance of a blood vessel, for example, as shown in FIGS. 27A, 27B, and 27C.

Figures 27C, 28:
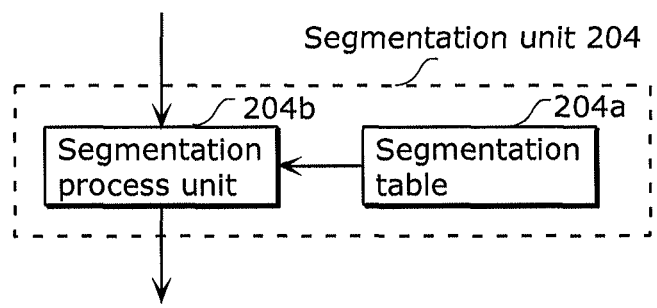
FIG. 27C is a diagram showing an example of the score translation table in the embodiment 3.
FIG. 28 is a block diagram of a detailed functional configuration of a segmentation unit according to the embodiment 3.

The adder 203e, for example, refers to a first score translation table shown in FIG. 27A to obtain a score (−1500, 0, or −600) corresponding to the result of the determination in step S231. Likewise, the adder 203e refers to, for example, a second score translation table shown in FIG. 27B to obtain a score corresponding to the Euclidean distance calculated in step S232. The adder 203e also refers to, for example, a third score translation table shown in FIG. 27C to obtain a score corresponding to the branch distance calculated in step S233.

Scores included in each score translation table are predetermined by, for example, statistical learning or the like.

In the first score translation table, scores are set so that a blood vessel object, if included in the fusional area, is of higher importance than if the blood vessel object is not included in the fusional area. Moreover, in the first score translation table, scores are set so that a blood vessel object, if located on the farther side than the fusional area, is of higher importance than if the blood vessel object is located on the nearer side than the fusional area.

In the second score translation table, scores are set so that a blood vessel object having a smaller spatial distance to the blood vessel object located at the point of gaze is of higher importance.

In the third score translation table, scores are set so that a blood vessel object having a less number of branches (the branch distance) to the blood vessel object located at the point of gaze is of higher importance.

The adder 203e further calculates the importance of the blood vessel object by adding the scores obtained in step S234 for each point on the blood vessel object (S235).

While in the present embodiment, the adder 203e refers to the score translation table to obtain scores, it should be noted that the adder 203e may obtain the scores using a predetermined transformation function.

FIG. 28 is a block diagram of a detailed functional configuration of the segmentation unit 204 according to the embodiment 3.

The segmentation unit 204 includes a segmentation table 204a and a segmentation process unit 204b.

In step S260, first, the segmentation process unit 204b refers to the segmentation table 204a to segment the three-dimensional image into a plurality of regions, in accordance with the importance levels of the blood vessel objects calculated in step S230.

For example, the segmentation process unit 204b refers to the segmentation table 204a shown in FIG. 29 to segment the area on the nearer side than the fusional area into two regions and segment the area on the farther side than the fusional area into three regions. It should be noted that the segmentation table 204a shown in FIG. 29 is an example. The segmentation unit 204 may include the segmentation table 204a for segmenting the three-dimensional image into more areas. Moreover, the segmentation unit 204 may segment the fusional area into a plurality of regions. Moreover, while in the present embodiment, a boundary value of importance for the segmentation is a fixed value, the boundary value may be adaptively changed in accordance with a distribution of importance levels or a distribution of depth values in the three-dimensional image.

While in the present embodiment, the area is segmented into a fixed number of regions, it should be noted that the number of areas into which the area is segmented may be changed in accordance with a range of the distribution of depths of the three-dimensional image, a size of the display range, or a size of the display screen.

In step S270, the correction process determination unit 205 refers to the segmentation table 204a to determine a correction process for each of the areas obtained by the segmentation in step S260.

In step S180, the image processing unit 206 generates a left-eye image and a right-eye image, in accordance with the correction process for each area determined in step S270. For an area the determined correction process on which is semi-transparentizing, the display color is made semitransparent when generating vertex coordinates of an object. On the other hand, for an area the determined correction process on which is one of blurring 1, 2, and 3, pixels are generated and then blurring by filtering is applied. The blurring 1 to 3 have different limited frequencies of a low pass filter. In the present embodiment, a limited frequency of the blurring 1 is the lowest, and a limited frequency of the blurring 3 is the highest.

Changing the correction process in accordance with the importance of a blood vessel as such can prevent fully hiding a blood vessel object that is, although located on the nearer side than the fusional area, useful to the viewer. Moreover, among the blood vessel objects located on farther sides than the fusional area, a blood vessel object that is useful to the viewer can be blurred by a reduced amount. Thus, the three-dimensional display device 200 determines a correction process in accordance with not only a depth but also the importance of a blood vessel object, thereby improving the visibility of a three-dimensional image, while avoiding the loss of information on an important blood vessel object which leads to a blood vessel object that is located at a point of gaze.

<Effects>

As described above, according to the three-dimensional display device 200 of the present embodiment, the visibility of a blood vessel object that not only has a small spatial distance to a blood vessel object which the viewer is gazing but also has high connectivity to the blood vessel object which the viewer is gazing can be improved. Thus, the visibility of a blood vessel object that is useful to the viewer can be improved. For example, the three-dimensional display device 200 can avoid the loss of information on a blood vessel object that has, although located outside the fusional area, a large connection with a blood vessel object which the use is gazing.

While in the present embodiment, the three-dimensional image is segmented in step S260 in accordance with the importance levels calculated in step S230, it should be noted that the three-dimensional image may not be segmented. In this case, the three-dimensional image may be corrected by transforming the importance levels into image processing parameters and performing image processing.

Embodiment 4

An embodiment 4 is different from the embodiment 3 in that the importance of a blood vessel is determined taking a state of a medical instrument, such as a catheter, into account.

Figure 30:
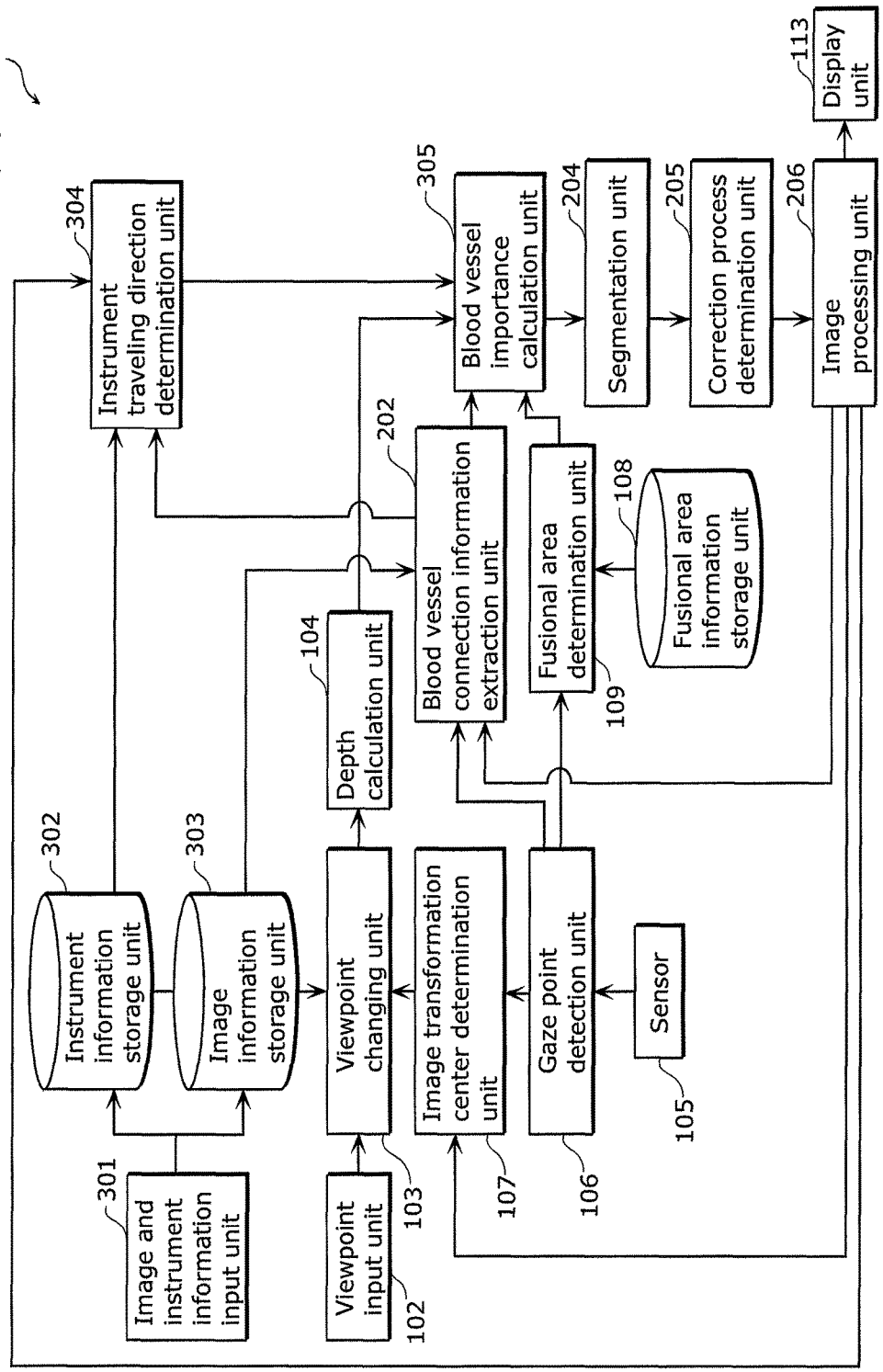
FIG. 30 is a block diagram of a functional configuration of a three-dimensional display device according to an embodiment 4.

FIG. 30 is a block diagram of a functional configuration of a three-dimensional display device 300 according to the embodiment 4.

The three-dimensional display device 300 includes an image information storage unit 303, a viewpoint input unit 102, a viewpoint changing unit 103, a depth calculation unit 104, a sensor 105, a gaze point detection unit 106, an image transformation center determination unit 107, a fusional area information storage unit 108, a fusional area determination unit 109, a blood vessel connection information extraction unit 202, a blood vessel importance calculation unit 305, a segmentation unit 204, a correction process determination unit 205, an image processing unit 206, a display unit 113, an instrument information storage unit 302, an instrument traveling direction determination unit 304, and an image and instrument information input unit 301.

The image and instrument information input unit 301 receives images of a blood vessel and a medical instrument, such as a catheter, when the medical instrument is being inserted into the blood vessel, and information (instrument information) on the medical instrument, and outputs them to the instrument information storage unit 302 and the image information storage unit 303. The images are input from an imaging device (not shown) such as a camera or X-ray imaging machine or a recording device (not shown). The instrument information is input from a control device (not shown) of the instrument, or an image processing system (not shown) or the like which obtains instrument information from the image of the instrument.

The instrument information storage unit 302 stores instrument information 302a which indicates, in a time sequence, positions of the leading end of a medical instrument, such as a catheter, which is advanced through a blood vessel. The image information storage unit 303 stores image information 303a. The image information 303a includes information which represents three-dimensional models of the blood vessel object and the instrument object in time series, and connection information which indicates connectivity between blood vessel objects.

Figure 32:
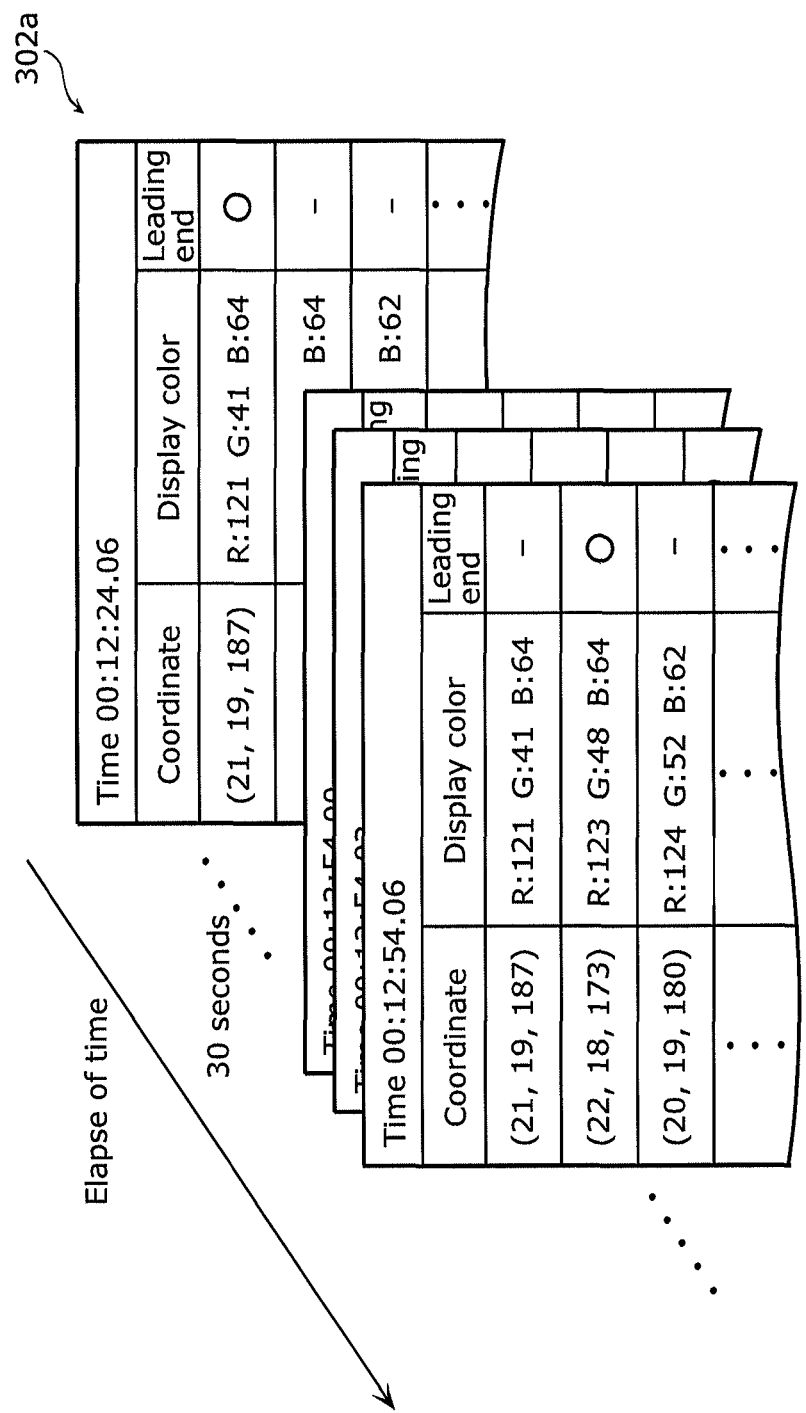
FIG. 32 is a diagram showing an example of instrument information in the embodiment 4.

FIG. 32 is a diagram showing an example of the instrument information 302a in the embodiment 4. As FIG. 32 shows, the instrument information 302a includes time information, coordinates of points on the blood vessel object and the instrument object in the standard coordinate system, a display color, and leading-end information which indicates a position of the leading end of the instrument object.

Figure 33:
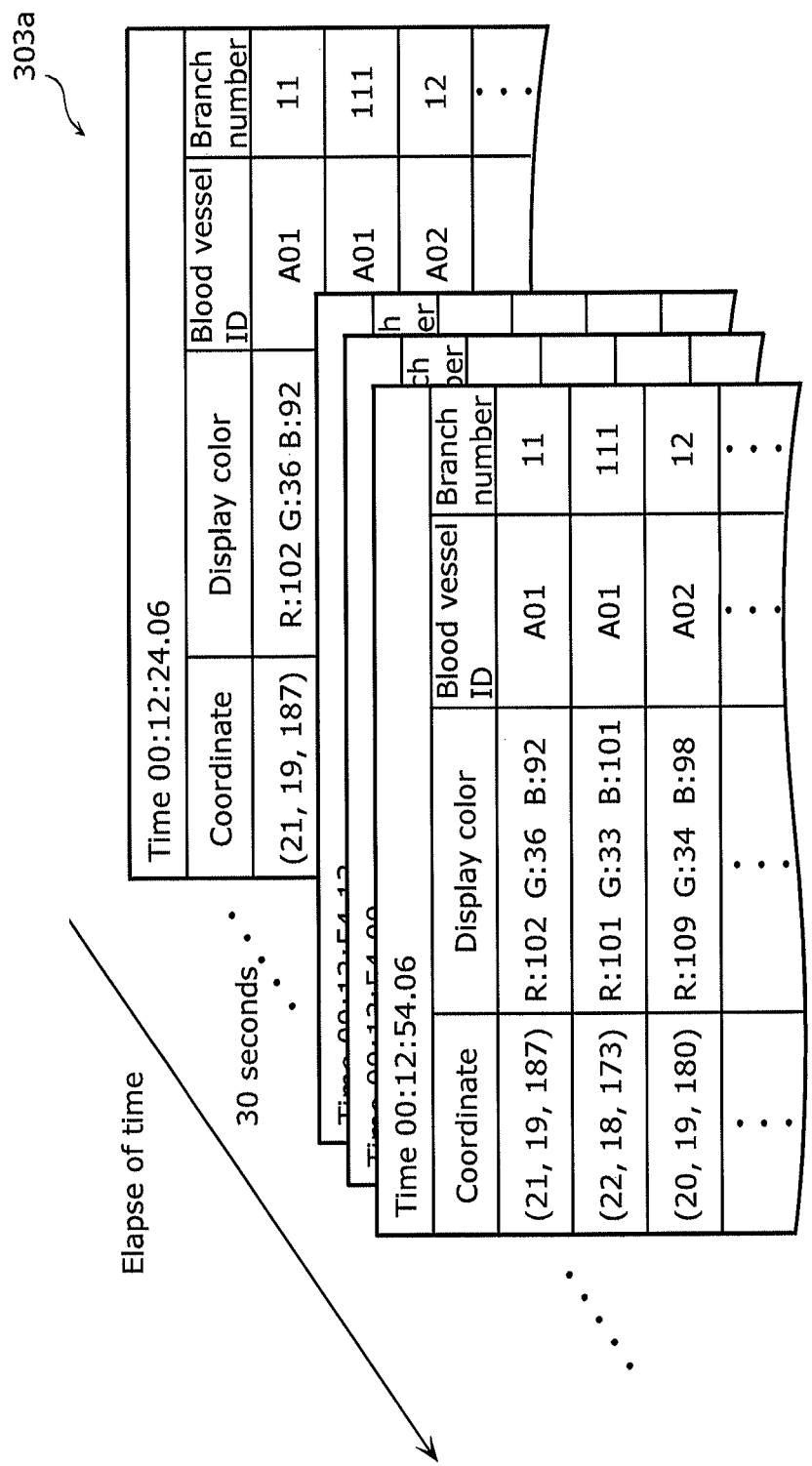
FIG. 33 is a diagram showing an example of image information in the embodiment 4.

FIG. 33 is a diagram showing an example of the image information 303a in the embodiment 4. As FIG. 33 shows, the image information 303a includes information, such as time information, coordinates of points on the blood vessel object and the instrument object in the standard coordinate system, a display color, a blood vessel ID, and a branch number of the blood vessel.

Here, the coordinates of points included in the image information 303a are the same as the coordinates of points included in the instrument information 302a. The image information 303a is synchronized in time with the instrument information 302a. It should be noted that the instrument information 302a and the image information 303a may not be time-series information and may be information at arbitrary time. In other words, the three-dimensional image may be a still image rather than a video.

The instrument traveling direction determination unit 304 is by way of example of an identification unit. The instrument traveling direction determination unit 304 determines a relationship of the instrument object with each blood vessel object, based on the position of the leading end of the instrument object indicated by the instrument information 302*a*. Specifically, the instrument traveling direction determination unit 304 identifies, among a plurality of blood vessel objects, a blood vessel object though which the instrument object has already passed, or a blood vessel object through which the instrument object does not pass.

Figure 31:
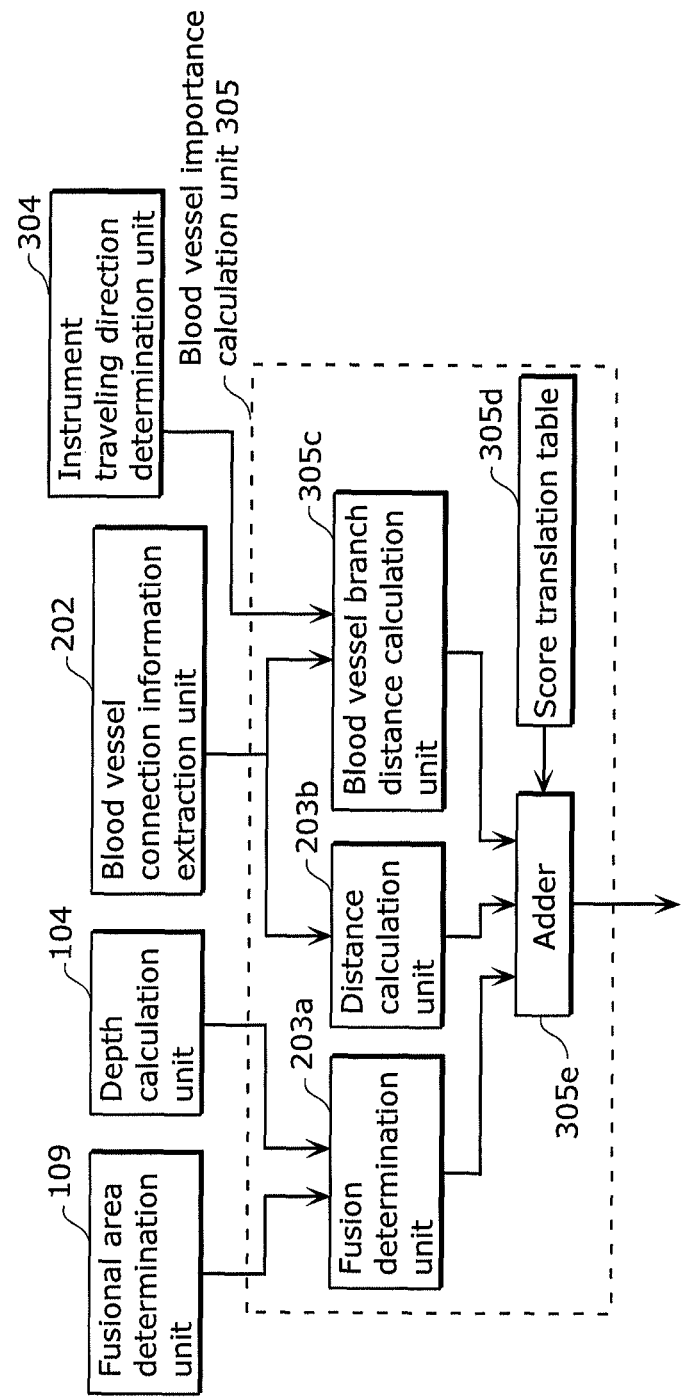
FIG. 31 is a block diagram of a detailed functional configuration of a blood vessel importance calculation unit according to the embodiment 4.

FIG. 31 is a block diagram of a detailed functional configuration of the blood vessel importance calculation unit 305 according to the embodiment 4.

The blood vessel importance calculation unit 305 includes the fusion determination unit 203*a*, the distance calculation unit 203*b*, the blood vessel branch distance calculation unit 305*c*, a score translation table 305*d*, and an adder 305*e*.

The blood vessel importance calculation unit 305 calculates the importance of a blood vessel object, based on a fusional area determined by the fusional area determination unit 109, a depth of the blood vessel object calculated by the depth calculation unit 104, connection information extracted by the blood vessel connection information extraction unit 202, and the information on the travel of the instrument determined by the instrument traveling direction determination unit 304.

The three-dimensional display device 300 according to the present embodiment is different from the embodiment 2 in the operation of the instrument traveling direction determination unit 304, and the operation of the blood vessel importance calculation unit 305 using output of the instrument traveling direction determination unit 304.

The instrument traveling direction determination unit 304, first, transforms coordinates of the instrument object as with the blood vessel object. Then, the instrument traveling direction determination unit 304 identifies a blood vessel object closest to a position of the leading end of the instrument object, as a blood vessel object having the instrument inserted therein.

For example, in FIG. 32, the leading end of the instrument object is at coordinates (22, 18, 173) at time 00:12:54.06. FIG. 33 indicates that a blood vessel object having a blood vessel ID "A01" and a branch number "111" is displayed at coordinates (22, 18, 173) at time 00:12:54.06.

The instrument traveling direction determination unit 304 refers to the image information 303*a* and the instrument information 302*a* to obtain a blood vessel ID and a branch number of the blood vessel object in which the leading end of the instrument object is present. The instrument traveling direction determination unit 304 refers to the instrument information 302*a* at a time backwards in time by a fixed time (e.g., 30 seconds) from the time at which the current displayed three-dimensional image is captured to obtain coordinates of a position of the leading end of the instrument object at that time backwards in time by the fixed time. The instrument traveling direction determination unit 304 identifies a blood vessel object in which the presence of the leading end of the instrument object at that time backwards in time by the fixed time is known, from the coordinates of the position of the leading end of the instrument object at the time backwards in time by the fixed time and the image information 303*a*.

In FIG. 32, for example, the instrument traveling direction determination unit 304 refers to the instrument information 302*a* at time 00:12:24.06 backwards in time by seconds from the time 00:12:54.06 to identify coordinates (21, 19, 187) indicating a position of the leading end of the instrument object 30 seconds prior to the time 00:12:54.06. Then, the instrument traveling direction determination unit 304 refers to the image information 303*a* of FIG. 33 to obtain a blood vessel ID "A01" and a branch number "11" of the blood vessel object at the coordinates (21, 19, 187) at the time 00:12:24.06. The instrument traveling direction determination unit 304 extracts a blood vessel object (in the example of FIG. 33, the blood vessel object having the blood vessel ID "A01" and the branch number "11") in which the presence of the leading end of the instrument object is known in the past, and a blood vessel object (in the example of FIG. 33, the blood vessel object having the blood vessel ID "A01" and the branch number "111") in which the leading end of the instrument object is currently present, and identifies a blood vessel ID and a branch number of a blood vessel object through which the leading end of the instrument object has already passed between the two time points. In the example of FIG. 33, the blood vessel object having the blood vessel ID "A01" and the branch number "11" and the blood vessel object having the blood vessel ID "A01" and the branch number "111" are the blood vessel objects through which the leading end of the instrument object has already passed.

The instrument traveling direction determination unit 304 further determines a blood vessel object through which the instrument object is likely to pass in the future, and a blood vessel object that is unrelated to the passage of the instrument object, using the identified blood vessel ID and the identified branch number. The blood vessel objects unrelated to the passage of the instrument object is a blood vessel object through which the instrument object does not pass. In other words, the blood vessel object unrelated to the passage of the instrument object is a blood vessel object through which the instrument object is unlikely to pass.

A blood vessel ID and a branch number include information whereby a blood vessel object from which each blood vessel object has branched off can be determined, for example, as shown in FIG. 22. In the example of FIG. 22, the instrument object passes through the blood vessel object that has the blood vessel ID "A01" and the branch number "11" and the blood vessel object that has the blood vessel ID "A01" and the branch number "111." Thus, it can be determined that the instrument object is advancing from the origin of the blood vessel in a direction in which the branch number increases.

Thus, the instrument traveling direction determination unit 304 determines blood vessel objects that have the blood vessel ID "A01," and branch numbers the first three digits of which are "111" as blood vessel objects through which the instrument object is likely to pass in the future. The instrument traveling direction determination unit 304 also determines the other blood vessel objects as the blood vessel object unrelated to the passage of the instrument object. The instrument traveling direction determination unit 304 outputs to the blood vessel importance calculation unit 305 information which indicates the blood vessel object through which the leading end of the instrument object has already passed, the blood vessel object through which the leading end of the instrument object is likely to pass in the future, and the blood vessel object unrelated to the passage of the leading end of the instrument object.

The blood vessel importance calculation unit 305 obtains the fusional area from the fusional area determination unit 109, obtains connection information from the blood vessel connection information extraction unit 202, and obtains the depths of the blood vessel objects from the depth calculation unit 104. Furthermore, the blood vessel importance calculation unit 305 obtains, from the instrument traveling direction determination unit 304, the information indicating the blood vessel object through which the leading end of the instrument object has passed, the blood vessel object through which the instrument object is likely to pass, and the blood vessel object unrelated to the passage of the instrument object.

A blood vessel branch distance calculation unit 305c, as with step S233 in the embodiment 3, calculates a branch distance. The blood vessel branch distance calculation unit 305c further attaches, to the blood vessel object having the branch distance calculated, the information that is output from the instrument traveling direction determination unit 304, indicating the blood vessel object through which the leading end of the instrument object has already passed, the blood vessel object through which the instrument object is likely to pass in the future, and the blood vessel object unrelated to the passage of the instrument object.

The adder 305e refers to the score translation table 305d to obtain scores, wherein the adder 305e performs processing to decrease scores of the blood vessel object through which the leading end of the instrument object has already passed and the blood vessel object unrelated to the passage of the instrument object, and increase scores of the blood vessel object through which the instrument, object is likely to pass in the future.

FIGS. 34A to 34E are diagrams showing examples of the score translation table 305d in the embodiment 4. The score translation table 305d includes, for example, a first score translation table of fusional area, a second score translation table of spatial distance, and third, fourth and fifth score translation tables of branch distances. The third, fourth and fifth score translation tables are thus classified based on relationships between the branch distances and the passage of the instrument object.

The first score translation table shown in FIG. 34A is the same as the first score translation table shown in FIG. 27A. The second score translation table shown in FIG. 34B is the same as the second score translation table shown in FIG. 27B.

The fourth score translation table illustrates, for example, branch distances of blood vessel objects through which the instrument object is likely to pass in the future. The third score translation table illustrates branch distances of blood vessel objects through which the instrument object has already passed. The fifth score translation table illustrates branch distances of blood vessel objects that are unrelated to the passage of the instrument object.

The adder 305e refers to the score translation table 305d to obtain a score for each point on the blood vessel object, using a result of the determination in step S231 of FIG. 26, a spatial distance calculated in step S232, the branch distance calculated by the blood vessel branch distance calculation unit 305c, and the classification information based on a passage status of the instrument object.

As FIG. 34D shows, in the fourth score translation table of the blood vessel objects through which the instrument object is likely to pass in the future, relatively high scores are associated with the branch distances. In contrast, as shown in FIG. 34C, in the third score translation table of the blood vessel objects through which the instrument object has already passed, lower scores than those in the fourth score translation table are associated with the branch distances. Also as shown in FIG. 34E, in the fifth score translation table of the blood vessel objects unrelated to the passage of the instrument object, lower scores than those in the third and fourth score translation tables are associated with the branch distances. For example, by obtaining a score associated with a branch distance using such a score translation table, the adder 305e can decrement scores of the branch distances of blood vessel objects through which the leading end of the instrument object has already passed, and the blood vessel objects unrelated to the passage of the instrument object, and increment scores of the branch distances of blood vessel objects through which the instrument object is likely to pass in the future.

As described above, according to the three-dimensional display device 300 of the present embodiment, the three-dimensional image can be corrected so as to suppress display of a blood vessel object through which the instrument object has already passed or display of a blood vessel object through which the instrument object does not pass. Thus, the three-dimensional display device 300 can prioritize display of a blood vessel object into which the instrument object is likely to be advanced, thereby displaying a useful three-dimensional image.

In the present embodiment, the instrument traveling direction determination unit 304 identifies the blood vessel object through which the leading end of the instrument object has already passed, the blood vessel object through which the leading end of the instrument object is likely to pass in the future, and the blood vessel object unrelated to the passage of the leading end of the instrument object. However, the instrument traveling direction determination unit 304 may not identify these three types of blood vessel objects. In other words, the instrument traveling direction determination unit 304 may identify at least one of the blood vessel object through which the leading end of the instrument object has already passed, the blood vessel object through which the leading end of the instrument object is likely to pass in the future, and the blood vessel object that is unrelated to the passage of the leading end of the instrument object.

Moreover, in the present embodiment, the three-dimensional display device does not correct an object in the fusional area. However, an enhancement process may be performed on a blood vessel object that is of particularly high importance in the fusional area. The enhancement process can be implemented by, for example, contrast enhancement, edge enhancement, or changing the display color.

This allows the three-dimensional display device to prioritize or enhance display of an image of an area of a blood vessel object in a direction of travel of the medical instrument in displaying a three-dimensional image of the blood vessel having the medical instrument, such as a catheter, inserted therein. Furthermore, the three-dimensional display device can downgrade a priority level of an area of the blood vessel through which the medical instrument has already passed, to process the image. This allows the three-dimensional display device to not only display merely a position of the blood vessel object on the three-dimensional display but also more naturally and clearly display a blood vessel object which the viewer needs to see.

Embodiment 5

Figure 35:
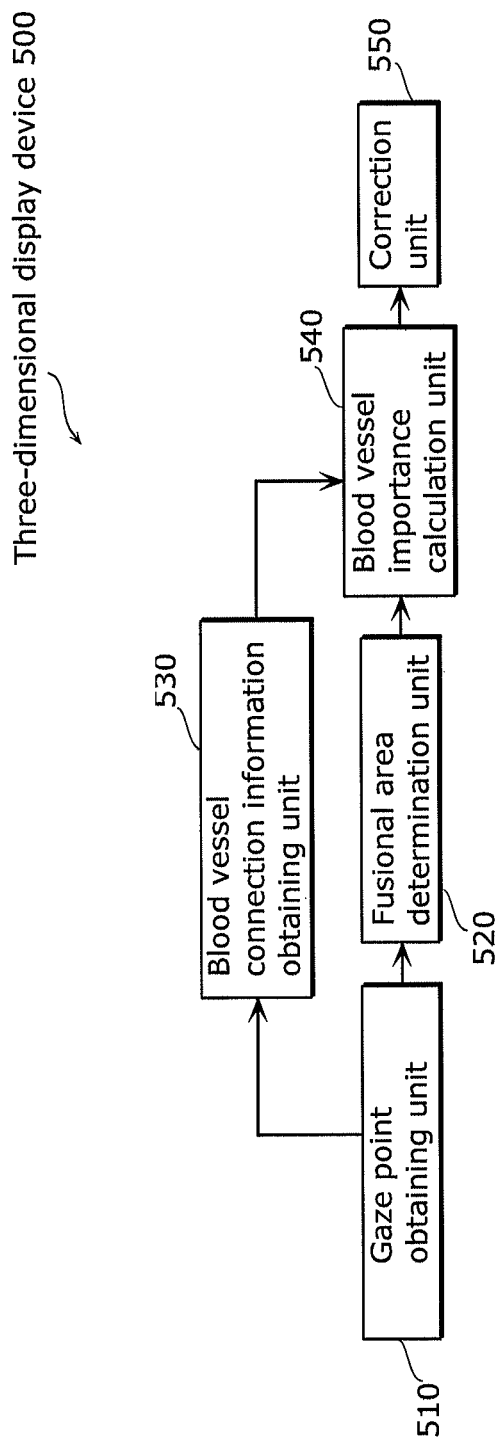
FIG. 35 is a block diagram of a functional configuration of a three-dimensional display device according to an embodiment 5.

FIG. 35 is a block diagram of a functional configuration of a three-dimensional display device 500 according to an embodiment 5.

The three-dimensional display device 500 includes a gaze point obtaining unit 510, a fusional area determination unit 520, a blood vessel connection information obtaining unit 530, a blood vessel importance calculation unit 540, and a correction unit 550.

The gaze point obtaining unit 510 obtains a point of gaze of a viewer. The gaze point obtaining unit 510 is input means represented by, for example, a pointing device such as a mouse and a touch panel. The viewer designates a point of gaze of the viewer in a displayed three-dimensional image. The gaze point obtaining unit 510 obtains the point designated by the viewer in the image, as the point of gaze. Moreover, the gaze point obtaining unit 510 may obtain the point of gaze by, for example, detecting a viewing direction of the viewer. It should be noted that the gaze point obtaining unit 510 may obtain the point of gaze by a method other than the above.

The fusional area determination unit 520 determines a fusional area, based on the obtained position of the point of gaze. The fusional area is an area where binocular fusion is allowed. Specifically, the fusional area determination unit 520 stores fusional area information which indicates, for example, positions of a plurality of points of gaze in the depth direction, and a plurality of fusional areas respectively corresponding to the positions of the plurality of points of gaze in the depth direction. In this case, the fusional area determination unit 520 refers to the fusional area information to determine a fusional area that corresponds to the obtained position of the point of gaze.

The blood vessel connection information obtaining unit 530, for example, obtains connection information of blood vessel objects in the three-dimensional image from a storage unit (not shown) storing blood vessel connection information or a recognition unit (not shown) which generates blood vessel connection information from the three-dimensional image.

The blood vessel importance calculation unit 540 calculates the importance of each of the blood vessel objects in the three-dimensional image, based on the fusional area determined by the fusional area determination unit 520, the blood vessel connection information obtained by the blood vessel connection information obtaining unit 530, and depth information of the blood vessel object.

The correction unit 550 corrects an image which is displayed according to the importance levels of the blood vessel objects output by the blood vessel importance calculation unit 540.

Figure 36:
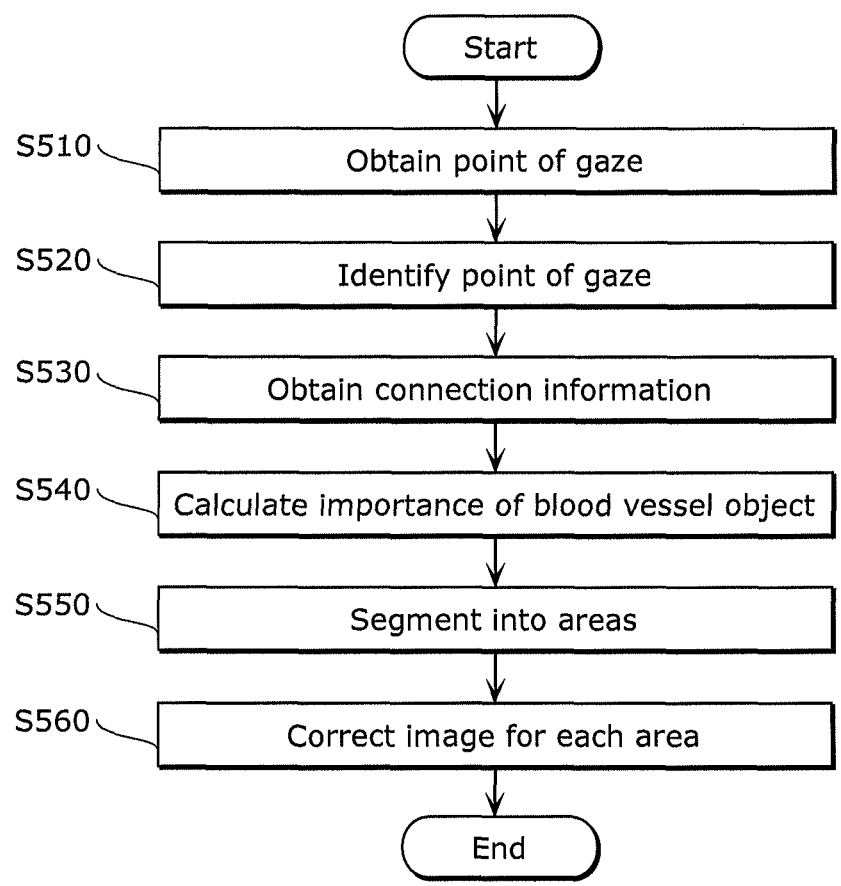
FIG. 36 is a flowchart illustrating processing operation of the three-dimensional display device according to the embodiment 5.

FIG. 36 is a flowchart illustrating processing operation of the three-dimensional display device 500 according to the embodiment 5. In accordance with, for example, a display start indication from the viewer input by display start input means not shown, the three-dimensional display device 500 starts the following processing:

First, the gaze point obtaining unit 510 obtains the three-dimensional image coordinates of a position of the point of gaze of the viewer in the three-dimensional image (S510). The blood vessel connection information obtaining unit 530 identifies the blood vessel object which the viewer is gazing, using the coordinates indicating the position of the point of gaze of the viewer obtained in step S510 and the currently displayed three-dimensional image (S520). Furthermore, the blood vessel connection information obtaining unit 530 obtains connection information indicating connectivity of the blood vessel object which the viewer is gazing to each of the blood vessel objects included in the three-dimensional image (S530). The blood vessel importance calculation unit 540 calculates the importance of each of the plurality of blood vessel objects included in the three-dimensional image, based on the connection information obtained in step S530 and a predetermined fusional area (S540). The correction unit 550 segments the three-dimensional image into a plurality of areas, based on the importance levels calculated in step S540 (S550). The correction unit 550 corrects the three-dimensional image for each area (S560).

As described above, according to the three-dimensional display device 500 of the present embodiment, the visibility of a blood vessel object that not only has a small spatial distance to a blood vessel object which the viewer is gazing but also has high connectivity to the blood vessel object which the viewer is gazing can be improved. Thus, the visibility of a blood vessel object that is useful to the viewer can be improved. For example, the three-dimensional display device 500 can avoid the loss of information on a blood vessel object that has, although located outside the fusional area, a large connection with a blood vessel object which the use is gazing.

While in the present embodiment, the blood vessel importance calculation unit 540 calculates the importance of a blood vessel object based on the blood vessel connection information and the fusional area, it should be noted that the blood vessel importance calculation unit 540 may calculate the importance of a blood vessel object so that the blood vessel object, if included in the fusional area, is of higher importance than if the blood vessel object is not included in the fusional area. This allows the three-dimensional display device 500 to display a natural image in which the blood vessel in the fusional area is less likely to be lost.

Embodiment 6

Figure 37:
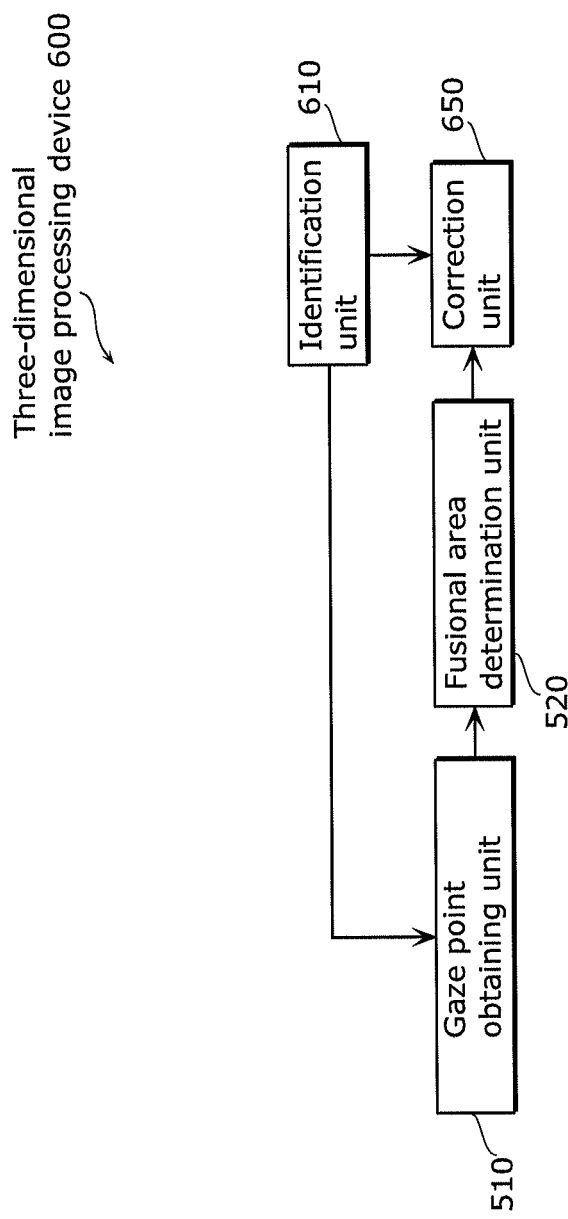
FIG. 37 is a block diagram of a functional configuration of a three-dimensional image processing device according to an embodiment 6.

FIG. 37 is a block diagram of a functional configuration of a three-dimensional image processing device 600 according to an embodiment 6.

The three-dimensional image processing device 600 includes a gaze point obtaining unit 510, a fusional area determination unit 520, an identification unit 610, and a correction unit 650.

The gaze point obtaining unit 510 obtains a point of gaze of a viewer. The gaze point obtaining unit 510 obtains a point in a displayed three-dimensional image as the point of gaze of the viewer. Examples of the method to obtain the point of gaze in the image include a method to obtain the point of gaze based on a viewer's, manipulation such as designating the point by a pointing device or designating the point by detecting a viewing direction, and a method to obtain a central point on a screen as the point of gaze. Moreover, the examples include a method to obtain a leading end of a medical instrument identified by the identification unit 610 as the point of gaze. The method to obtain the point of gaze may be other than the above.

The fusional area determination unit 520 determines a fusional area where binocular fusion is allowed, based on the obtained position of the point of gaze.

The identification unit 610 determines a relationship of the instrument, object with each, of the blood vessel objects, based on a position of the leading end of the instrument object in a displayed three-dimensional image. Specifically, the identification unit 610 identifies, among a plurality of blood vessel objects, a blood vessel object through which the instrument object has already passed or a blood vessel object through which the instrument object does not pass.

The correction unit 650 obtains the output of the fusional area determination unit 520 and the output of the identification unit 610. The correction unit 650 corrects the image so as to suppress display of blood vessel objects outside the fusional area and, additionally, suppress display of the blood vessel object through which the instrument object has already passed that is identified by the identification unit 610 in the displayed three-dimensional image.

As described above, according to the three-dimensional image processing device 600 of the present embodiment, the image can be corrected not only so as to improve the visibility of a blood vessel object that has a close spatial distance to the point of gaze of the viewer, but also so as to suppress display of a blood vessel object through which the medical instrument, such as a catheter, has already passed and improve the visibility of the blood vessel object through which the medical instrument is likely to pass in the future.

Other Embodiment

While the three-dimensional display device according to only one or more aspects has been described with reference to the exemplary embodiments, the present disclosure is not limited to the embodiments. Various modifications to the embodiments that may be conceived by those skilled in the art and combinations of components of different embodiments are intended to be included within the scope of the one or more aspects, without departing from the spirit of the present disclosure.

For example, while in the above embodiments 2 to 4, the three-dimensional display device performs the series of operations when viewpoint operation is input to the viewpoint input unit 102, the three-dimensional display device may perform the series of operations if a movement of the point of gaze by a certain amount or greater is input. This allows the three-dimensional image to be corrected appropriately in accordance with the movement of the point of gaze, and the visibility of the three-dimensional image to be improved without requiring the viewer to input operation.

It should be noted that each component in each embodiment may take the form as dedicated hardware or may be implemented by executing a software program suitable for each component. The component may be implemented by a program execution unit, such as or CPU or processor, loading and executing the software program stored in a recording medium such as a hard disk or a semiconductor memory. Here, the software program for implementing the three-dimensional display device according to the above embodiments is the following program.

Specifically, the program causes a computer to execute a three-dimensional display method including: obtaining a position of a gaze point of a viewer; determining a fusional area where binocular fusion is allowed, based on the obtained position of the gaze point; correcting the three-dimensional image so as to suppress display of an object which is included in the three-dimensional image outside the fusional area; and displaying the corrected three-dimensional image.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

A three-dimensional image device according to one or more exemplary embodiments disclosed herein is useful as a display device for displaying a three-dimensional image or a three-dimensional video, and, in particular, useful for televisions, computers, game machines, and so on.

The invention claimed is:

1. A three-dimensional display device for displaying a three-dimensional image, comprising:
   a gaze point obtaining unit configured to obtain a position of a gaze point of a viewer;
   a fusional area determination unit configured to determine a fusional area where binocular fusion is allowed, based on the obtained position of the gaze point;
   a correction unit configured to correct the three-dimensional image so as to suppress display of an object which is included in the three-dimensional image outside the fusional area;
   a display unit configured to display the corrected three-dimensional image; and
   a fusional area information storage unit configured to store fusional area information which indicates positions of a plurality of gaze points in a depth direction of the three-dimensional image and a plurality of fusional areas corresponding to the positions of the plurality of gaze points in the depth direction,
   wherein the fusional area determination unit is configured to refer to the fusional area information to determine the fusional area that corresponds to the obtained position of the gaze point.

2. The three-dimensional display device according to claim 1,
   wherein the correction unit is configured to correct the three-dimensional image by removing an object which is included in the three-dimensional image and located on a side closer to the viewer than the fusional area is.

3. The three-dimensional display device according to claim 1,
   wherein the correction unit is configured to correct the three-dimensional image by blurring an object which is included in the three-dimensional image and located on a side farther away from the viewer than the fusional area is.

4. The three-dimensional display device according to claim 1, further comprising
   a viewpoint changing unit configured to change a viewpoint of the three-dimensional image so that a display position of an object which is included in the three-dimensional image and located at the position of the gaze point does not change in a depth direction,
   wherein the correction unit is configured to correct the three-dimensional image the viewpoint of which has been changed.

5. The three-dimensional display device according to claim 4,
   wherein changing the viewpoint is a process of rotating the three-dimensional image about the position of the gaze point.

6. A three-dimensional display device for displaying a three-dimensional image, comprising:
   a gaze point obtaining unit configured to obtain a position of a gaze point of a viewer;
   a fusional area determination unit configured to determine a fusional area where binocular fusion is allowed, based on the obtained position of the gaze point;
   a correction unit configured to correct the three-dimensional image so as to suppress display of an object which is included in the three-dimensional image outside the fusional area; and
   a display unit configured to display the corrected three-dimensional image,
   wherein the three-dimensional image includes a plurality of blood vessel objects representing a plurality of blood vessels,
   three-dimensional display device further comprising:
   a blood vessel connection information obtaining unit configured to obtain connection information indicating connectivity of a blood vessel object located at the gaze point to each of the blood vessel objects included in the three-dimensional image; and a blood vessel importance calculation unit configured to calculate importance of each of the blood vessel objects included in the three-dimensional image, based on the fusional area and the connection information, wherein the correction unit is configured to correct the three-dimensional image so that display of a blood vessel object the importance of which is lower is suppressed to a greater extent.

7. The three-dimensional display device according to claim 6, wherein the blood vessel importance calculation unit is configured to calculate, for each of the blood vessel objects, the importance of the blood vessel object so that the blood vessel object, if included in the fusional area, is of higher importance than if the blood vessel object is not included in the fusional area.

8. The three-dimensional display device according to claim 6, wherein the blood vessel importance calculation unit is configured to calculate, for each of the blood vessel objects, the importance of the blood vessel object so that the blood vessel object having a less number of blood vessel branches to the blood vessel object located at the gaze point is of higher importance.

9. The three-dimensional display device according to claim 6, wherein the blood vessel importance calculation unit is configured to calculate, for each of the blood vessel objects, the importance of the blood vessel objects so that the blood vessel object having a smaller spatial distance to the blood vessel object located at the gaze point is of higher importance.

10. A three-dimensional display device for displaying a three-dimensional image, comprising:

a gaze point obtaining unit configured to obtain a position of a gaze point of a viewer;

a fusional area determination unit configured to determine a fusional area where binocular fusion is allowed, based on the obtained position of the gaze point;

a correction unit configured to correct the three-dimensional image so as to suppress display of an object which is included in the three-dimensional image outside the fusional area; and a display unit configured to display the corrected three-dimensional image, wherein the three-dimensional image includes a plurality of blood vessel objects representing a plurality of blood vessels, and an instrument object representing a medical instrument which is advanced through at least one of the blood vessel objects, the three-dimensional display device further comprising an identification unit configured to identify, among the plurality of blood vessel objects, a blood vessel object through which the instrument object has already passed or a blood vessel object through which the instrument object does not pass, wherein the correction unit is configured to correct the three-dimensional image so as to suppress display of a blood vessel object which is located outside the fusional area and through which the instrument object has already passed or display of a blood vessel object which is located outside the fusional area and through which the instrument object does not pass.

11. A three-dimensional display method for displaying a three-dimensional image, comprising:

obtaining a position of a gaze point of a viewer;

determining a fusional area where binocular fusion is allowed, based on the obtained position of the gaze point;

correcting the three-dimensional image so as to suppress display of an object which is included in the three-dimensional image outside the fusional area; and displaying the corrected three-dimensional image, wherein the three-dimensional image includes a plurality of blood vessel objects representing a plurality of blood vessels, and an instrument object representing a medical instrument which is advanced through at least one of the blood vessel objects, the three-dimensional display method further comprising identifying, among the plurality of blood vessel objects, a blood vessel object through which the instrument object has already passed or a blood vessel object through which the instrument object does not pass, wherein said correcting comprises correcting the three-dimensional image so as to suppress display of a blood vessel object which is located outside the fusional area and through which the instrument object has already passed or display of a blood vessel object which is located outside the fusional area and through which the instrument object does not pass.

12. A non-transitory computer-readable recording medium storing a program for causing a computer to execute the three-dimensional display method according to claim 11.

13. A three-dimensional image processing device for processing a three-dimensional image including a plurality of blood vessel objects representing a plurality of blood vessels, and an instrument object representing a medical instrument which is advanced through at least one of the blood vessel objects, the three-dimensional image processing device comprising:

a gaze point obtaining unit configured to obtain a position of a gaze point of a viewer;

a fusional area determination unit configured to determine a fusional area where binocular fusion is allowed, based on the obtained position of the gaze point;

an identification unit configured to identify, among the plurality of blood vessel objects, a blood vessel object through which the instrument object has already passed or a blood vessel object through which the instrument object does not pass; and a correction unit configured to correct the three-dimensional image so as to suppress display of a blood vessel object which is located outside the fusional area and through which the instrument object has already passed or display of a blood vessel object which is located outside the fusional area and through which the instrument object does not pass.

* * * * *